(12) United States Patent
Kitagawa

(10) Patent No.: US 9,229,017 B2
(45) Date of Patent: Jan. 5, 2016

(54) SAMPLE PROCESSING APPARATUS, TRANSPORT APPARATUS AND NON-TRANSITORY STORAGE MEDIUM

(75) Inventor: Nobuhiro Kitagawa, Akashi (JP)

(73) Assignee: SYSMEX CORPORATION, Kobe-Shi (JP)

( * ) Notice: Subject to any disclaimer, the term of this patent is extended or adjusted under 35 U.S.C. 154(b) by 17 days.

(21) Appl. No.: 12/978,094

(22) Filed: Dec. 23, 2010

(65) Prior Publication Data

US 2011/0158851 A1 Jun. 30, 2011

(30) Foreign Application Priority Data

Dec. 28, 2009 (JP) .................... 2009-298587

(51) Int. Cl.
*G01N 35/02* (2006.01)
*G01N 35/04* (2006.01)
*G01N 35/00* (2006.01)
*G01N 1/31* (2006.01)

(52) U.S. Cl.
CPC ............ *G01N 35/0092* (2013.01); *G01N 35/04* (2013.01); *G01N 1/312* (2013.01); *G01N 2035/0094* (2013.01); *G01N 2035/00752* (2013.01); *G01N 2035/0415* (2013.01); *G01N 2035/0462* (2013.01); *G01N 2035/0472* (2013.01)

(58) Field of Classification Search
CPC .............. G01N 2035/0462; G01N 2035/0415; G01N 2035/0094
See application file for complete search history.

(56) References Cited

U.S. PATENT DOCUMENTS

| 2005/0196320 | A1* | 9/2005 | Veiner et al. ..................... 422/63 |
| 2007/0009920 | A1* | 1/2007 | Burchell ........................... 435/6 |
| 2008/0310999 | A1* | 12/2008 | Yagi et al. ........................ 422/65 |
| 2009/0035185 | A1 | 2/2009 | Tsujimura et al. |
| 2011/0076193 | A1* | 3/2011 | Kitagawa et al. ............... 422/65 |

FOREIGN PATENT DOCUMENTS

| CN | 101118245 | A | | 2/2008 |
| CN | 101430339 | A | | 5/2009 |
| JP | 63-217273 | A | | 9/1988 |
| JP | 3-94159 | A | | 4/1991 |
| JP | 06-148202 | A | | 5/1994 |
| JP | 9-54095 | A | | 2/1997 |
| JP | 2001-074754 | A | | 3/2001 |
| JP | 2007-309743 | A | | 11/2007 |
| JP | 2008-032652 | | * | 2/2008 |

* cited by examiner

*Primary Examiner* — P. Kathryn Wright
(74) *Attorney, Agent, or Firm* — Brinks Gilson & Lione

(57) ABSTRACT

A transport apparatus includes: a first transport line configured to transport a rack downstream along the transporting route; a second transport line configured to transport the rack upstream along the transporting route; and a controller including a processor and a memory that stores programs executable by the processor to: determine where to transport a post-tested rack according to whether or not retesting is necessary on any sample held in the post-tested rack; and according to a determination, instruct the transport apparatus to transport the post-tested rack selectively (i) along the first transport line either back to first sample processing unit, where the rack has been tested, or to a second sample processing unit located downstream of the first sample processing unit, or (ii) along the second transport line back from the first sample processing unit.

11 Claims, 14 Drawing Sheets

FIG. 11

| RACK ID | HOLDING POSITION | SAMPLE ID | CBC | DIFF | RET | SP |
|---|---|---|---|---|---|---|
| 1 | 1 | P121 | 1 | 1 | 0 | 0 |
| 1 | 2 | P122 | 1 | 0 | 0 | 0 |
| ⋮ | ⋮ | ⋮ | ⋮ | ⋮ | ⋮ | ⋮ |
| 1 | 9 | P129 | 1 | 1 | 0 | 0 |
| 1 | 10 | P130 | 1 | 1 | 0 | 0 |

FIG. 12

| RACK ID | HOLDING POSITION | SAMPLE ID | CBC | DIFF | RET | SP |
|---|---|---|---|---|---|---|
| 1 | 1 | P121 | 0 | 0 | 0 | 0 |
| 1 | 2 | P122 | 0 | 0 | 0 | 0 |
| ⋮ | ⋮ | ⋮ | ⋮ | ⋮ | ⋮ | ⋮ |
| 1 | 9 | P129 | 0 | 0 | 0 | 0 |
| 1 | 10 | P130 | 0 | 0 | 0 | 0 |

FIG. 13

| RACK ID | HOLDING POSITION | SAMPLE ID | CBC | DIFF | RET | SP |
|---|---|---|---|---|---|---|
| 1 | 1 | P121 | 0 | 0 | 1 | 1 |
| 1 | 2 | P122 | 0 | 0 | 0 | 0 |
| ⋮ | ⋮ | ⋮ | ⋮ | ⋮ | ⋮ | ⋮ |
| 1 | 9 | P129 | 0 | 0 | 1 | 0 |
| 1 | 10 | P130 | 0 | 0 | 0 | 1 |

SAMPLE PROCESSING APPARATUS, TRANSPORT APPARATUS AND NON-TRANSITORY STORAGE MEDIUM

RELATED APPLICATIONS

This application claims priority under 35 U.S.C. §119 to Japanese Patent Application No. 2009-298587 filed on Dec. 28, 2009, the entire content of which is hereby incorporated by reference.

FIELD OF THE INVENTION

The present invention relates to an apparatus and a non-transitory storage medium for processing a sample, for example, measure components of the sample and prepare a smear sample thereof, and a sample container transporting apparatus which transports a sample container containing the sample to carry out the process on the sample.

BACKGROUND OF THE INVENTION

Conventionally a sample processing system provided with a plurality of sample processing apparatuses such as a multi-channel blood cell analyzer or a blood smear sample preparing apparatus is known. The sample processing system transports a sample supplied by a user to these sample processing apparatuses and collects the sample already processed by the sample processing apparatuses.

Japanese Laid-Open Patent Publication No. 2001-74754 discloses an automatic analyzer provided with a rack setting unit where a rack holding a sample container is set, a sample feed transport line, a rack supply/collection unit which supplies the rack set in the rack setting unit to the sample feed transport line, a sample return transport line, a rack storage unit, and a plurality of analysis units. The automatic analyzer transports the rack supplied by the rack supply/collection unit in a feed direction using the sample feed transport line to analyze a target sample by any selected one of the plurality of analysis units. The post-analysis rack is transported in a return direction opposite to the feed direction by the sample return transport line and collected by the rack supply/collection unit, and then transported to and stored in the rack storage unit. The automatic analyzer disclosed in Japanese Laid-Open Patent Publication No. 2001-74754 is structurally advantageous in that the rack setting unit and the rack storage unit are provided on the same side apart from the analysis units. This structure allows the user to supply (load) and collect the sample in one place.

Japanese Laid-Open Patent Publication No. H06-148202 discloses an automatic analyzer which has a sample supply unit where a sample rack is set, a transport line used to transport the sample rack supplied at a predetermined transport start position by the sample supply unit, a reaction unit which suctions a given volume of the sample from a sample container held in the sample rack transported to a predetermined suctioning position to perform a predefined test to the suctioned sample, return lines used to return the sample rack from which the samples are already suctioned, a sorting mechanism which sorts the sample rack to one of the return lines, a return mechanism which returns the sample rack returned by the return line selectively to the transport start position, and a rack storage unit which stores therein the test-completed sample rack. In the automatic analyzer disclosed in Japanese Laid-Open Patent Publication No. H06-148202, the sample supply unit and the rack storage unit are provided on the same side apart from the reaction unit, and the sample rack to be retested is transported again to the transport start position by the return mechanism, whereas the sample racks which are not to be tested are transported to the rack storage unit.

In the automatic analyzer disclosed in the Japanese Laid-Open Patent Publication No. 2001-74754, if the sample held in the rack supplied from the rack supply/collection unit is analyzed by at least two analysis units, the sample is suctioned at the sample suctioning position in one of the analysis units to be analyzed there, and then further transported to the sample suctioning position of the other analysis unit to be suctioned and analyzed there. However, no regard is given to retesting (reanalysis) in the automatic analyzer.

In the automatic analyzer disclosed in Japanese Laid-Open Patent Publication No. H06-148202, the sample rack holding the sample to be retested is transported to the exit of the transport line similarly to the sample rack which holds only the samples which need not be retested, and then transported by the return line in a direction opposite to the transport direction of the transport line back to the transport start position again. Thus, the sample rack has to travel a long transport path, which is a bottleneck in improving the efficiency of retest. In the case where a sample is currently suctioned from any other sample rack by the reaction unit on the downstream side of the transport direction, for example, it is necessary to suspend the transport of the sample rack to be retested until the suctioning is over, which causes clogging on the transport path. Whenever the traffic on the transport path is thus clogged, the retesting efficiency is significantly deteriorated.

SUMMARY OF THE INVENTION

The scope of the present invention is defined solely by the appended claims, and is not affected to any degree by the statements within this summary.

A first aspect of the present invention is a sample processing apparatus comprising: a plurality of sample processing units arranged along a line of transporting route, the plurality of sample processing units comprising a sample processing unit configured to test a sample held in a rack and issue a test result on the sample; a sample feeding unit located upstream of the plurality of sample processing units along the transporting route and configured to store pre-tested racks waiting to be tested; a collecting unit located upstream of the plurality of sample processing units along the transporting route and configured to store post-tested racks; a transport apparatus comprising a first transport line configured to transport the rack downstream along the transporting route from the sample feeding unit and a second transport line configured to transport the rack upstream along the transporting route toward the collecting unit; and a controller comprising a processor and a memory that stores programs executable by the processor to: determine where to transport the post-tested rack according to whether or not retesting is necessary on any sample held in the post-tested rack; and according to a determination, instruct the transport apparatus to transport the post-tested rack selectively (i) along the first transport line either back to a first sample processing unit, where the sample in the rack has been tested, or to a second sample processing unit located downstream of the first sample processing unit, or (ii) along the second transport line back to the collecting unit from the first sample processing unit.

A second aspect of the present invention is a transport apparatus for transporting racks with samples along a transporting route along which a plurality of sample processing units are arranged, comprising: a first transport line configured to transport a rack downstream along the transporting route; a second transport line configured to transport the rack upstream along the transporting route; and a controller comprising a processor and a memory that stores programs executable by the processor to: determine where to transport a post-tested rack according to whether or not retesting is necessary on any sample held in the post-tested rack; and according to a determination, instruct the transport apparatus to transport the post-tested rack selectively (i) along the first transport line either back to first sample processing unit, where the rack has been tested, or to a second sample processing unit located downstream of the first sample processing unit, or (ii) along the second transport line back from the first sample processing unit.

A third aspect of the present invention is at least one non-transitory storage medium which stores programs executable collectively by at least one processor to: transport a pre-tested rack to a first sample processing unit for testing which is selected among a plurality of sample processing units arranged along a transporting route; receive a test result for the rack from the first sample processing unit; based on the test result, determine whether or not retesting is necessary on any sample held in the post-tested rack; if it is determined that retesting is necessary, transport the post-tested rack either back to the first sample processing unit or to a second testing unit located downstream of the first testing unit along the transporting route; and if it is determined that retesting is not necessary, transport the post-tested rack back along the transporting route from the first sample processing unit.

BRIEF DESCRIPTION OF THE DRAWINGS

FIG. 11 is a schematic illustration of measurement orders of pre-measurement samples stored in a test information management apparatus;

FIG. 12 is a schematic illustration of measurement orders of post-measurement samples stored in the test information management apparatus;

FIG. 13 is a schematic illustration of measurement orders of post-analysis samples stored in the test information management apparatus;

DETAILED DESCRIPTION OF THE EMBODIMENTS

Figure 1:
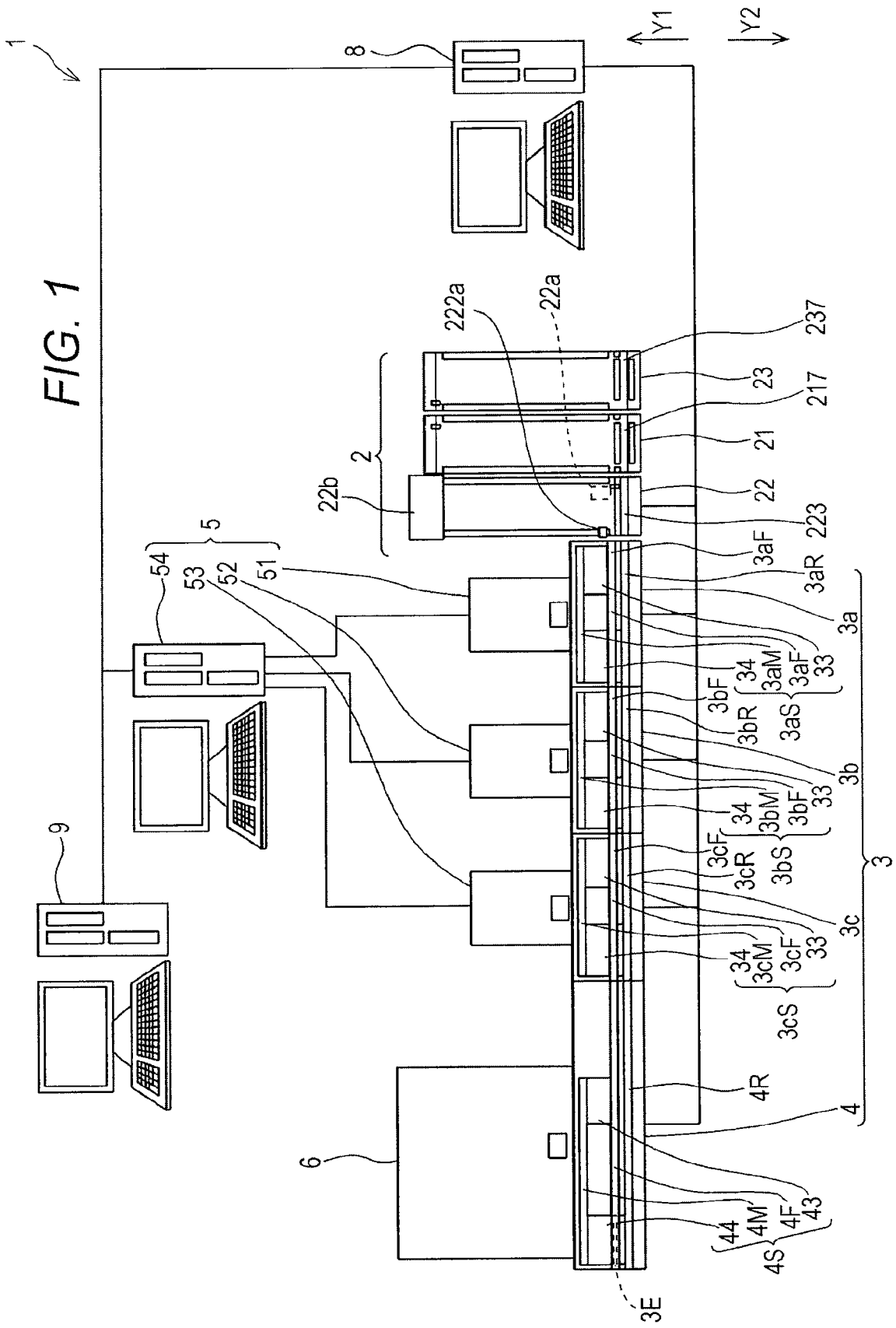
FIG. 1 is a schematic plan view of an overall structure of a sample processing system according to an embodiment of the present invention.

An embodiment of the present invention is described below referring to the drawings.

[Structure of Sample Processing System]

FIG. 1 is a schematic plan view of an overall structure of a sample processing system according to an embodiment of the present invention. As illustrated in FIG. 1, a sample processing system 1 is provided with a sample loading and collection apparatus 2, a sample transport apparatus 3, a blood cell analysis apparatus 5, a smear sample preparing apparatus 6, and a system controller 8. The sample processing system 1 according to the present embodiment is connected to a test information management apparatus 9 through a communication network to allow communication with the test information management apparatus 9.

The sample transport apparatus 3 has sample transport units 3a, 3b, 3c, and 4, and these sample transport units 3a, 3b, 3c, and 4 are serially connected to one another so as to linearly extend in lateral directions of the drawing. The blood cell analysis apparatus 5 has three measurement units 51, 52, and 53, and an information processing unit 54. The measurement unit 51 is provided behind the sample transport unit 3a, the measurement unit 52 is provided behind the sample transport unit 3b, and the measurement unit 53 is provided behind the sample transport unit 3c. The smear sample preparing apparatus 6 is provided behind the sample transport unit 4.

The sample transport units 3a, 3b, 3c, and 4 are respectively provided with supply lines 3aS, 3bS, 3cS, and 4S (first transport line) used as transport paths to transport a sample rack so that samples housed therein are supplied to the measurement units 51, 52, and 53 and the smear sample preparing apparatus 6 (sample processing unit), which are all laterally extending. The sample transport apparatus 3 is further provided with return lines 3aR, 3bR, 3cR, and 4R (second transport path) used as transport paths to transport the sample rack rightward in the drawing to be collected. The supply line 3aS includes a measurement line 3aM (fetching line) laterally extending, and a skipping line 3aF which transports the sample rack holding a plurality of samples leftward in the drawing. The other supply lines 3bS, 3cS and 4S similarly have measurement lines 3bM and 3cM, a processing line 4M, skipping lines 3bF and 3cF and a transport line 4F. The measurement lines 3aM, 3bM, and 3cM and the processing line 4M are the transport paths for transporting the sample rack so that the measurement units 51, 52, and 53 and the smear sample preparing apparatus 6 can fetch the samples housed therein. The measurement lines 3aM, 3bM, and 3cM and the processing line 4M are independent from one another with no connection therebetween. The skipping lines 3aF, 3bF, and 3cF and the transport line 4F are the transport paths for transporting the sample rack directly toward the downstream side of the transport direction while skipping the sample fetch by any of the measurement units 51, 52, and 53 and the smear sample preparing apparatus 6. Of the skipping lines 3aF, 3bF, and 3cF and the transport line 4F, the adjacent lines are connected to each other. All of these lines are linearly aligned.

Between the skipping lines 3aF, 3bF, 3cF and the transport line 4F, and the measurement lines 3aM, 3bM, and 3cM and the processing line 4M, there are pre-analysis rack holding sections 33 and 43 (first relay sections) serving as transport paths for receiving the sample rack from the skipping lines 3aF, 3bF, 3cF and the transport line 4F and transporting the received sample rack to starting points of the measurement lines 3aM, 3bM, and 3cM and the processing line 4M, and also as regions for holding the sampler rack, and post-analysis rack holding sections 34 and 44 (second relay sections) serving as transport paths for receiving the sample rack from terminal points of the measurement lines 3aM, 3bM, and 3cM and the processing line 4M and transporting the received sample rack to the skipping lines 3aF, 3bF, and 3cF and the transport line 4F or the return lines 3aR, 3bR, 3cR, and 4R, and also as regions for holding the sample rack. The pre-analysis analysis rack holding sections 33 and 43, and the post-analysis analysis rack holding sections 34 and 44 (second relay sections) also constitute a part of the supply lines 3aS, 3bS, 3cS, and 4S.

The sample loading and collection apparatus 2 where the sample rack is loaded by a user is connected to the right end of the sample transport apparatus 3. The sample rack discharged from the sample loading and collection apparatus 2 is transported along the skipping line 3aF, 3bF, 3cF or 4F of the sample transport apparatus 3. The sample rack transported along the skipping line 3aF, 3bF, 3cF or 4F passes through the pre-analysis rack holding section 33 or 43 in the sample transport unit 3a, 3b, 3c, or 4 corresponding to a transport destination which is the measurement unit 51, 52, or 53 or the smear sample preparing apparatus 6. The sample rack is then transported to the measurement line 3aM, 3bM, 3cM or the processing line 4M. The sample rack is transported on the measurement line or the processing line, and then supplied to the measurement unit 51, 52, 53 or the smear sample preparing apparatus 6 serving as the destination. After the sample is supplied to the measurement unit 51, 52, 53 or the smear sample preparing apparatus 6, the sample rack travels along the measurement line 3aM, 3bM, 3cM or the processing line 4M and passes through the post-analysis rack holding section 34 or 44. The sample rack is then transported to the return line 3aR, 3bR, 3cR, or 4R, and further transported on the return line rightward to be collected by the sample loading and collection apparatus 2.

Figure 2:
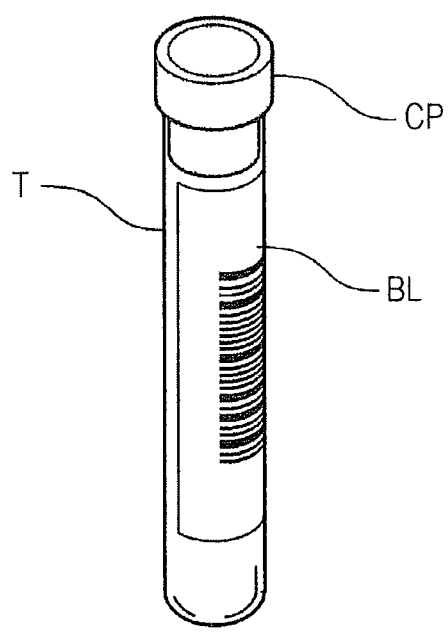
FIG. 2 is a perspective view of an external appearance of a sample container.
Figure 3:
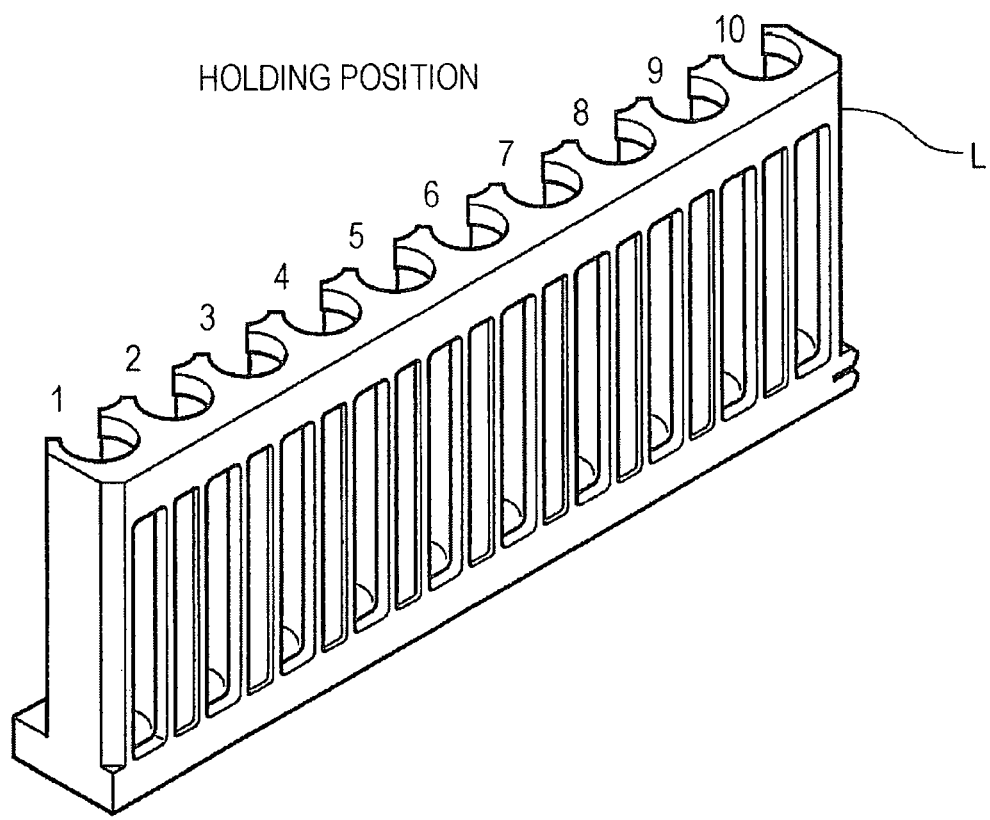
FIG. 3 is a perspective view of an external appearance of a sample rack.

FIG. 2 is a perspective view of an external appearance of a sample container. FIG. 3 is a perspective view of an external appearance of a sample rack. As illustrated in FIG. 2, a sample container T has a tubular shape, and an upper end thereof is open. The sample container contains therein blood collected from a patient as a sample, and its upper-end opening is sealed with a cap portion CP. The sample container T is made of optically transparent glass or synthetic resin so that the blood sample inside is visible. A barcode label BL is affixed to a side surface of the sample container T. The barcode label BL has a barcode (sample barcode) representing a sample ID printed thereon. A sample rack L can hold 10 sample containers T in an aligned manner. The sample rack L holds the sample containers T perpendicularly (upright position). A rack barcode label (not illustrated in the drawings) is affixed to a front surface of the sample rack L. The rack barcode label has a barcode (rack barcode) representing a rack ID printed thereon.

Hereinafter, the structural elements of the sample processing system 1 are described in detail.

<Structure of Sample Loading and Collection Apparatus 2>

As illustrated in FIG. 1, the sample loading and collection apparatus 2 includes a sample loading unit 21, a pre-processing unit 22, and a sample collection unit 23. The sample loading and collection apparatus 2 can set therein a sample rack holding a plurality of sample containers.

The sample loading unit 21 can load therein the sample rack L supplied by a user. The sample loading unit 21 can transfer the sample rack L loaded by the user to the rearmost side of the sample loading unit 21 (Y1 direction) and transport the sample rack L to the left side of the sample loading unit 21 (to the side of the pre-processing unit 22).

The pre-processing unit 22 is connected to the left side of the sample loading unit 21 to receive the sample rack L dispatched from the sample loading unit 21. The pre-processing unit 22 has a barcode readout device 22b. The barcode readout device 22b can read out the sample ID from the barcode label BL of the sample container T set in the sample rack L and also read out the rack ID from the rack barcode label of the sample rack L. The pre-processing unit 22 can transfer the sample rack L already barcode-read by the barcode readout device 22b to the front side of the pre-processing unit 22 (Y2 direction) and thereafter transport the sample rack L to the left side of the pre-processing unit 22 (to the side of the sample transport unit 3a). In the vicinity of a rack delivering position between the pre-processing unit 22 and the sample transport unit 3a, a dedicated barcode readout device 222a for reading out the rack barcode of the sample rack L is provided. The sample rack L dispatched from the pre-processing unit 22 is guided to the skipping line 3aF of the sample transport apparatus 3. The pre-processing unit 22 has a controller 22a including such structural components as a CPU and a memory. The controller 22a controls the mechanism of the pre-processing unit 22.

The sample collection unit 23 is provided on the right side of the sample loading unit 21 and has a structure similar to that of the sample loading unit 21. The sample collection unit 23 collects the sample rack L transported thereto by the return line 3aR, or the collection line 223, 217, 237.

[Structure of Sample Transport Apparatus 3]

The structural characteristic of the sample transport apparatus 3 is described below. As illustrated in FIG. 1, the sample processing system 1 has the sample transport apparatus 3 including four sample transport units 3a, 3b, 3c, and 4. The sampler transport units 3a, 3b, and 3c are respectively provided on the front side of three measurement units 51, 52, and 53 of the blood cell analysis apparatus 5. Of the sample transport units 3a, 3b, and 3c, the adjacent sample transport units are connected to each other so that the sample rack L can be passed and received therebetween. The rightmost sample transport unit 3a is connected to the sample loading and collection apparatus 2 to receive the sample rack L transported from the sample loading and collection apparatus 2 and send the sample rack L back to the sample loading and collection apparatus 2.

Figure 4:
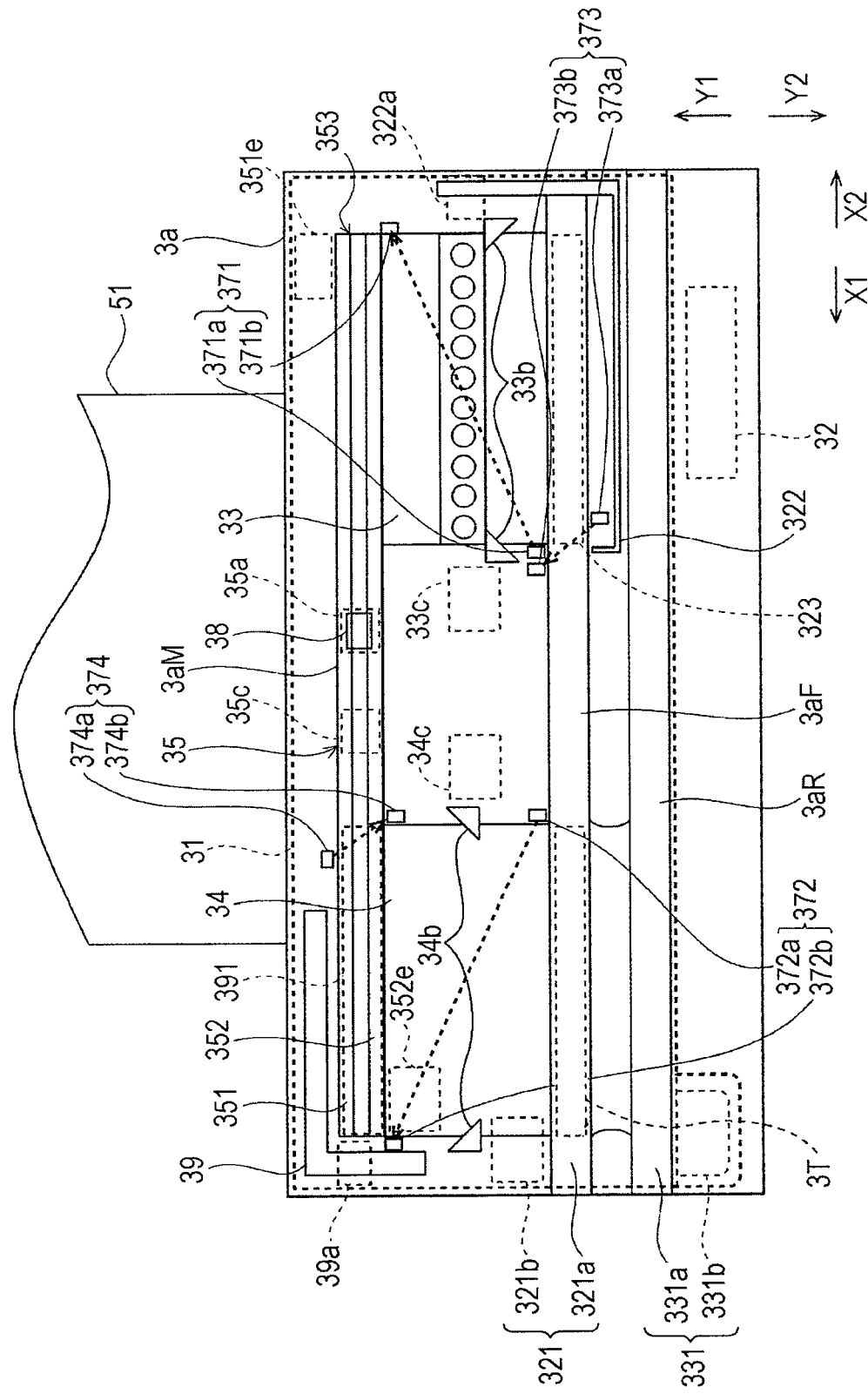
FIG. 4 is a plan view illustrating a structure of a sample transport unit used in a blood analysis apparatus according to the embodiment.

FIG. 4 is a plan view illustrating a structure of the sample transport unit 3a. Hereinafter, the sample transport unit 3a disposed on the front side of the measurement unit 51 is described. The description given below is also applied to structures of the other sample transport units 3b and 3c disposed on the front side of the measurement units 52 and 53. As illustrated in FIG. 4, the sample transport unit 3a has a transport mechanism 31, and a controller 32 which controls the transport mechanism 31. The transport mechanism 31 has a pre-analysis rack holding section 33, a post-analysis rack holding section 34, a measurement line 3aM (fetching line) which horizontally transfers the sample rack L in the direction of arrow X in the drawing and transports the sample rack L received from the pre-analysis rack holding section 33 to the post-analysis rack holding section 34 in order to supply the sample to the measurement unit 51, a skipping line 3aF which accepts the sample rack L from the apparatus on the transport upstream side (sample loading and collection apparatus 2) and transports the sample rack L to the apparatus on the transport downstream side (sample transport unit 3b) without supplying the samples contained in the sample rack L to the measurement unit 51, and a return line 3aR (second transport line) which accepts the sample rack L from the apparatus on the transport downstream side (sample transport unit 3b) and transports the sample rack L to the apparatus on the transport upstream side (sample loading and collection apparatus 2) without supplying the samples contained in the sample rack L to the measurement unit 51.

The skipping line 3aF has a belt conveyer 321 having an annular belt 321a and a stepping motor 321b. The belt conveyer 321 rotates the belt 321a in the direction of arrow X1 using a driving force of the stepping motor 321b to thereby transfer the sample rack L disposed on the belt 321a in the direction of X1. The skipping lines 3aF, 3bF, and 3cF of the sample transport units 3a, 3b, and 3c, and the transport line 4F of the sample transport unit 4 which will be described later each similarly includes a belt conveyer, and the sample rack L can be transported by the respective belt conveyers.

The return line 3aR in parallel with the skipping line 3aF is provided away from the skipping line 3aF by a given distance in the forward direction. The return line 3aR has a belt conveyer 331 having an annular belt 331a and a stepping motor 331b. The belt conveyer 331 rotates the belt 331a in the direction of arrow X2 using a driving force of the stepping motor 331b to thereby transfer the sample rack L disposed on the belt 331a in the direction of X2. The return lines 3aR, 3bR, and 3cR of the sample transport units 3a, 3b, and 3c, and the return line 4R of the sample transport unit 4 which will be described later each similarly includes a belt conveyer, and the sample rack L can be transported by the respective belt conveyers.

On the front side of the pre-analysis rack holding section 33, a rack delivering portion 322 is provided between the skipping line 3aF and the return line 3aR so as to face the pre-analysis rack holding section 33. The rack delivering portion 322 is horizontally transferred in a linear manner in the direction of Y1 (rearward) by a driving force of the stepping motor 322a. Accordingly, when the sample rack L is transported by the skipping line 3aF from the apparatus on the upstream side of the transport direction and arrives at a position 323 on the skipping line 3aF between the pre-analysis rack holding section 33 and the rack delivering portion 322 (hereinafter, called "pre-analysis rack delivering position"), the rack delivering portion 322 is transferred to the side of the pre-analysis rack holding section 33 to push the sample rack L into the pre-analysis rack holding section 33. The sample transport unit 3a is equipped with a rack sensor 373 which detects the sample rack L that arrived at the pre-analysis rack delivering position 323. The rack sensor 373 has a photoemitter 373a and a photoreceiver 373b.

The pre-analysis rack holding section 33 has a rectangular shape in planar view. The lateral length of the pre-analysis rack holding section 33 is slightly larger than that of the sample rack L. The width of the pre-analysis rack holding section 33 (length in front-back direction) is slightly larger than twice the width of the sample rack L. The pre-analysis rack holding section 33 is formed in a height lower than any other surface around it, and the pre-analysis sample rack L is disposed on an upper surface thereof. According to the structure, the pre-analysis rack holding section 33 can hold two sample racks L at a time. The pre-analysis rack holding section 33 is continuous to the skipping line 3aF so that the sample rack L is delivered thereto from the skipping line 3aF by the rack delivering portion 322. In the vicinity of the pre-analysis rack holding section 33, a rack sensor 371 is mounted, and the sample rack L placed in the pre-analysis rack holding section 33 is detected by the rack sensor 371. The rack sensor 371 is an optical sensor, having a photoemitter 371a and a photoreceiver 371b. The photoemitter 371a is provided on a lateral side of the pre-analysis rack holding section 33, while the photoreceiver 371b is provided on a straight line which traverses the pre-analysis rack holding section 33 slantwise toward its front side from the photoemitter 371a. The photoemitter 371a is positioned so that light is emitted diagonally forward, and the photoreceiver 371b is positioned to be able to receive the emitted light. Therefore, the sample rack L transported from the skipping line 3aF is placed in the pre-analysis rack holding section 33, and the sample rack L thus placed blocks the light emitted from the photoemitter 371a to lower the light reception of the photoreceiver 371b. As a result, the sample rack L can be detected by the rack sensor 371. The pre-analysis rack holding section 33 has rack senders 33b protruding inward from the both surfaces thereof. When the sample rack L is detected by the rack sensor 371, the rack senders 33b shift rearward (direction toward the measurement line 3aM) to be engaged with the sample rack L, and thereby transport the sample rack L rearward. The rack senders 33b can be driven by a stepping motor 33c provided below the pre-analysis rack holding section 33.

On the transport path where the sample rack L is transported by the measurement line 3aM, there are a sample container detecting position 35a at which the sample container is detected by a sample container sensor 38, and a sample supply position 35c (sample fetching position) at which the sample is supplied to the measurement unit 51 of the blood cell analysis apparatus 5. The measurement line 3aM can be used to transport the sample to the sample supply position 35c by way of the sample container detecting position 35a. The sample supply position 35c is a position provided on the downstream side of the transport direction away from the sample container detecting position 35a by a dimension equal to one sample. When the sample is transported to the sample supply position 35c by the measurement line 3aM, a hand portion of the measurement unit 51 of the blood cell analysis apparatus 5, which will be described later, grips the sample container T containing the sample to take the sample container T out of the sample rack L. Then, the sample is suctioned from the sample container T and supplied to the measurement unit 51. After the sample container is transported to the sample supply position 35c along the measurement line 3aM, the sample transport unit 3a temporarily suspends the transport of the sample rack L until the sample container T is returned to the sample rack L after the supply of the sample is finished.

The measurement line 3aM includes a belt conveyer 353 having a first belt 351 and a second belt 352 which independently operate, a stepping motor 351e which drives the first belt 351, and a stepping motor 352e which drives the second belt 352.

A rack delivering section 39, which will be described later, is provided so as to face the post-analysis rack holding section 34 with the measurement line 3aM interposed therebetween. The rack delivering section 39 is horizontally moved in the direction of arrow Y in a linear manner by a driving force of a stepping motor 39a. Accordingly, when the sample rack L is transported to a position 391 between the post-analysis rack holding section 34 and the rack delivering section 39 (hereinafter, called "post-analysis rack delivering position"), the rack delivering section 39 is moved to the side of the post-analysis rack holding section 34 to push the sample rack L into the post-analysis rack holding section 34. As described, the analysis-completed sample rack L is transported from the measurement line 3aM to the post-analysis rack holding section 34. The sample transport unit 3a is provided with a rack sensor 374 which detects the sample rack which arrived at the post-analysis rack delivering position 391. The rack sensor 374 has a photoemitter 374a and a photoreceiver 374b.

The post-analysis rack holding section 34 has a rectangular shape in planar view. The lateral length of the post-analysis rack holding section 34 is slightly larger than that of the sample rack L, and its width (length in front-back direction) is slightly larger than twice the width of the sample rack L. The post-analysis rack holding section 34 is formed in a height lower than any other surface around it, and the analysis-completed sample rack L is disposed on an upper surface thereof. According to the structure, the post-analysis rack holding section 34 can hold two sample racks L at a time. The post-analysis rack holding section 34 is continuous to the measurement line 3aM so that the sample rack L is delivered thereto from the measurement line 3aM by the rack delivering section 39. In the vicinity of the post-analysis rack holding section 34, a rack sensor 372 is mounted, and the sample rack L placed in the post-analysis rack holding section 34 is detected by the rack sensor 372. The rack sensor 372 is an optical sensor, having a photoemitter 372a and a photoreceiver 372b. The photoemitter 372a is provided on a lateral side of the post-analysis rack holding section 34, while the photoreceiver 372b is provided on a straight line which traverses the post-analysis rack holding section 34 slantwise toward its front side from the photoemitter 372a. The photoemitter 372a is positioned so that light is emitted diagonally forward, and the photoreceiver 372b is positioned to be able to receive the emitted light. Therefore, the sample rack L transported from the rack delivering section 39 is placed in the post-analysis rack holding section 34, and the sample rack L thus placed blocks the light emitted from the photoemitter 372a to lower the light reception level of the photoreceiver 372b. As a result, the sample rack L can be detected by the rack sensor 372. The post-analysis rack holding section 34 has rack senders 34b protruding inward from the both surfaces thereof. When the sample rack L is detected by the rack sensor 372, the rack senders 34b shift forward (direction toward the skipping line 3aF and return line 3aR) to be engaged with the sample rack L, and thereby transport the sample rack L forward. The rack senders 34b can be driven by a stepping motor 34c provided below the post-analysis rack holding section 34. Further, the post-analysis rack holding section 34 is continuous to the skipping line 3aF and the return line 3aR. According to the structure, the rack senders 34b can transport the sample rack L placed in the post-analysis rack holding section 34 to one of the skipping line 3aF and the return line 3aR. The rack senders 34b transport the sample rack L placed in the post-analysis rack holding section 34 to a position 3T (hereinafter, called "rack transport position") on the skipping line 3aF on the front side of the post-analysis rack holding section 34. The rack senders 34b can transfer the sample rack L placed in the post-analysis rack holding section 34 to the return line 3aR by way of the rack transport position 3T.

The transport mechanism 31 structurally characterized as described so far is mostly controlled by the controller 32. The controller 32 includes such structural elements as CPU, ROM and RAM (not illustrated in the drawing). The controller 32 can run a control program of the transport mechanism 31 stored in the ROM on the CPU. The controller 32 is equipped with an Ethernet (registered trademark) interface and connected to the information processing unit 54 and the system controller 8 via LAN.

Of the structural elements of the transport mechanism 31, the rack senders 33b, the belt conveyer 353 constituting the measurement line 3aM, and the rack delivering section 39 are controlled by the information processing unit 54 of the blood cell analysis apparatus 5. The other structural elements of the transport mechanism 31 are controlled by the controller 32.

According to the structure thus far described, the sample transport unit 3a (3b, 3c) can transport the sample rack L transported from the sample loading and collection apparatus 2 to the pre-analysis rack delivering position 323 along the skipping line 3aF, transport the sample rack L to the pre-analysis rack holding section 33 using the rack delivering portion 322, and then transfer the sample rack L from the pre-analysis rack holding section 33 to the measurement line 3aM and further transport the sample rack L on the measurement line 3aM to finally supply the sample to the measurement unit 51 (52, 53). The sample rack L containing the sample that has finished the suction is transported to the post-analysis rack delivering position 391 by the measurement line 3aM, and then transported to the post-analysis rack holding section 34 by the rack delivering section 39. The sample rack L held by the post-analysis rack holding section 34 is transported to the return line 3aR in the case where none of the samples held therein needs retesting, and then transported to the apparatus (sample loading and collection apparatus 2) in the former stage (upstream side of the transport direction) along the return line 3aR. On the other hand, the sample rack L holding any sample which needs to be retested is transported to one of the measurement units 51, 52, and 53 and the smear sample preparing apparatus 6 along the supply line 3aS, 3bS, 3cS, or 4S to be retested (reprocessed) by the apparatus of the transport destination.

When the sample rack L holding any sample to be processed by the measurement unit 52 or 53 on the transport downstream side or the smear sample preparing apparatus 6 is received from the apparatus in the former stage by the sample transport unit 3, the received sample rack L is transported along the skipping line 3aF in the direction of arrow X1 to be directly transported to the sample transport unit 3b in the latter stage. When the sample rack L to be collected by the sample loading and collection apparatus 2 is received from the sample transport unit 3b in the latter stage by the sample transport unit 3a, the received sample rack L is transported along the return line 3aR of the sample transport unit 3a in the direction of arrow X2 to be directly transported to the sample loading and collection apparatus 2 in the former stage.

As illustrated in FIG. 1, the sample transport unit 4 is disposed on the front side of the smear sample preparing apparatus 6. Of the three sample transport units 3a, 3b, and 3c, the sample transport unit 3c at the farthest end of the transport downstream side (left side in the drawing) is connected to the right end of the sample transport unit 4.

Figure 5:
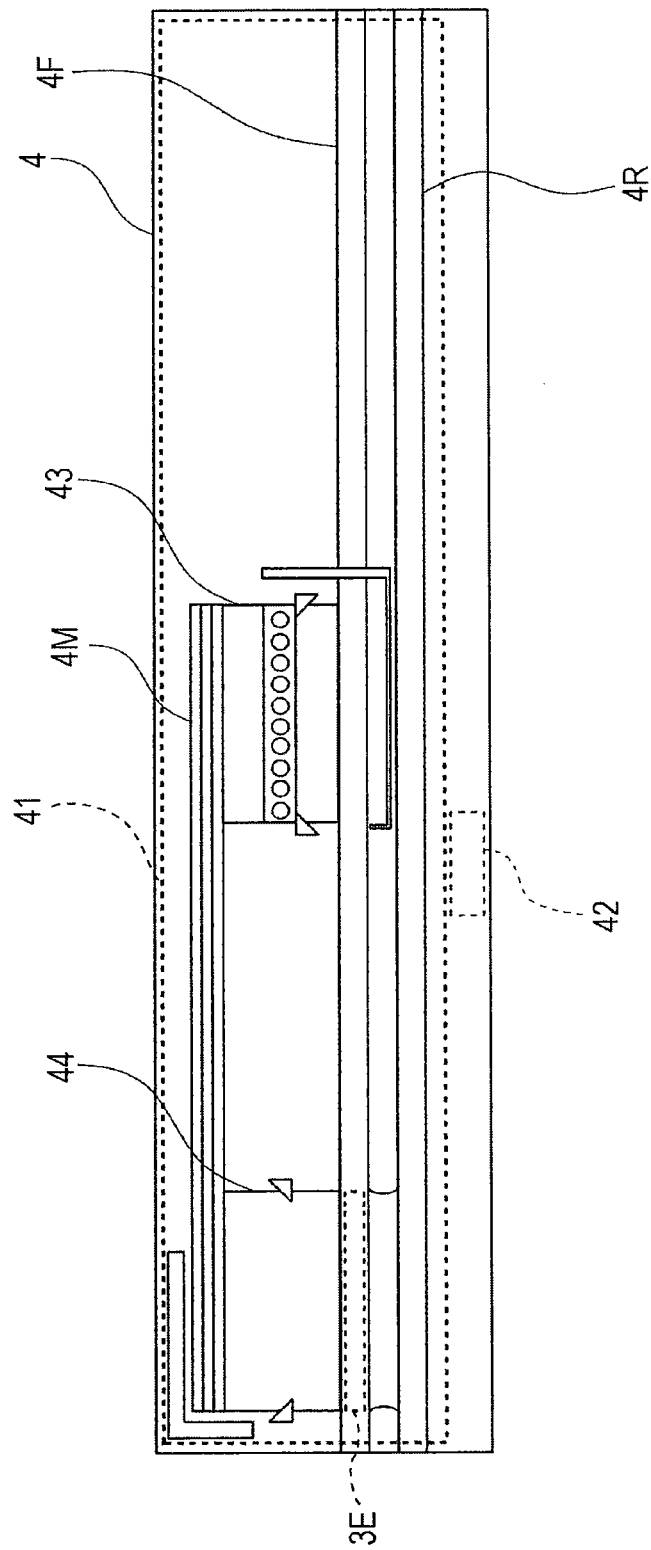
FIG. 5 is a plan view illustrating a structure of a sample transport unit used in a smear sample preparing apparatus according to the embodiment.

FIG. 5 is a plan view illustrating a structure of the sample transport unit 4. The sample transport unit 4 has a transport mechanism 41 which transports a sample, and a controller 42 which controls the transport mechanism 41. The transport mechanism 41 has a pre-process rack holding section 43 capable of temporarily holding the sample rack L which holds the sample containers T containing the samples from which no smear sample is yet prepared, a post-process rack holding section 44 capable of temporarily holding the sample rack L which holds the sample containers T from which the samples have been suctioned by the smear sample preparing apparatus 6, a processing line 4M which horizontally moves the sample rack L in a linear manner in the direction of X1 to supply the sample rack L received from the pre-process rack holding section 43 to the post-process rack holding section 44 in order to supply the sample to the smear sample preparing apparatus 6, a transport line 4F which accepts the sample rack L from the sample transport unit 3c on the transport upstream side and transports the sample rack L in the direction of X1, and a return line 4R which transports the sample rack L to the sample transport unit 3c on the transport upstream side in order to collect the sample rack L for which the smear sample preparation is completed by the sample loading and collection apparatus 2. The structural elements of the sample transport apparatus 4 have dimensions, shapes and positions different to those of the sample transport units 3a, 3b, and 3c. However, they are functionally similar to the sample transport units 3a, 3b, and 3c. Therefore, description of these structural elements is omitted.

The sample transport unit 4 accepts the sample rack L transported from the sample transport unit 3c on the upstream side using the transport line 4F, transfers the sample rack L to the pre-process rack holding section 43 using a rack delivering section not illustrated in the drawing, and then transports the sample rack L from the pre-process rack holding section 43 to the processing line 4M to transport the sample rack L along the processing line 4M so that the sample rack L is finally transported to the smear sample preparing apparatus 6. The sample rack L containing the sample that has finished the suction is transported by the processing line 4M to the post-process rack holding section 44 by a rack delivering section not illustrated in the drawing. The sample rack L held by the post-process rack holding section 44 is transferred to the return line 4R, and transported along the return line 4R to the sample transport unit 3c in the former stage (upstream side of the transport direction).

A left-end position of the transport line 4F of the sample transport unit 4, in other words, a position on the front side of the post-process rack holding section 44 is a terminal position 3E of the supply lines 3aS, 3bS, 3cS and 4S (first transport line). The sample rack L which holds any sample for which the smear sample preparation is necessary is transported along the supply line 4S of the sample transport unit 4, and the sample is supplied to the smear sample preparing apparatus 6. After that, the sample rack L passes through the post-analysis rack holding section 44 by way of the terminal point 3E. Then, the sample rack L is transferred to the return line 4R and transported along the return line 4R in the direction of X2 to be collected by the sample collection unit 23.

[Structure of Blood Cell Analysis Apparatus 5]

The blood cell analysis apparatus 5 is a multichannel blood cell analysis apparatus which uses optical flow cytometry. A side scattered light intensity and a fluorescence intensity, for example, of blood cells included in blood collected as a sample are obtained to classify the blood cells included in the sample into different types based on the obtained light intensities. Further, the blood cells of different types are separately counted, and a scattergram in which the blood cells thus classified are shown in different colors is created and displayed. The blood cell analysis apparatus 5 has measurement units 51, 52, and 53 which measure blood collected as a sample, and an information processing unit 54 which processes measurement data outputted from the measurement units 51, 52, and 53 and displays an analysis result of the blood sample.

As illustrated in FIG. 1, the blood cell analysis apparatus 5 has three measurement units 51, 52, and 53 and one information processing unit 54. The information processing unit 54 is connected to the three measurement units 51, 52, and 53 to allow communication therebetween. The information processing unit 54 can control the operations of the three measurement units 51, 52, and 53. The information processing unit 54 is also connected to the three sample transport units 3a, 3b, and 3c disposed on the front side of the three measurement units 51, 52, and 53 so as to communicate therewith.

Figure 6:
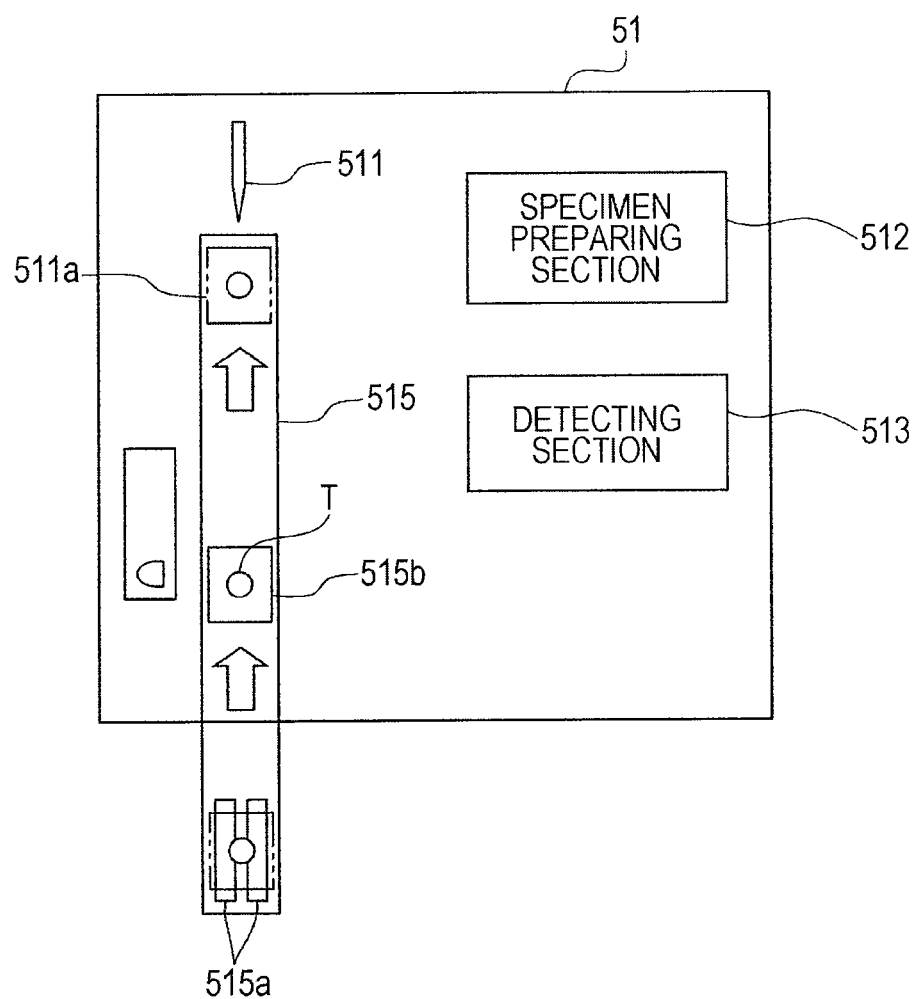
FIG. 6 is a block diagram illustrating a structure of a measurement unit provided in the blood analysis apparatus according to the embodiment.

FIG. 6 is a block diagram illustrating a structure of the measurement unit 51. As illustrated in FIG. 6, the measurement unit 51 has a sample suctioning section 511 which suctions the blood sample from the sample container (blood collection tube) T, a specimen preparing section 512 which prepares a measurement specimen from the blood suctioned by the sample suctioning section 511, and a detecting section 513 which detects blood cells in the measurement specimen prepared by the specimen preparing section 512. The measurement unit 51 further has a fetching port (not illustrated in the drawing) through which the sample container T held in the sample rack L transported on the measurement line 3aM of the sample transport unit 3a is fetched into the measurement unit 51, and a sample container transport section 515 which fetches the sample container T into the measurement unit 51 from the sample rack L and transports the fetched sample container T to a suctioning position where the sample is suctioned by the sample suctioning section 511.

The detecting section 513 can detect RBC (red blood cells) and PLT (platelets) by employing sheath flow DC detection. The detecting section 513 can also detect HGB (hemoglobin) by employing SLS-hemoglobin method and detect WBC (white blood cells) by employing flow cytometry in which a semiconductor laser is used. The RBC, PLT, HGB, and WBC are measured when CBC (complete blood count) is requested.

The measurement unit 51 can classify the white blood cells into five categories (measurement item DIFF). More specifically, the detecting section 513 of the measurement unit 51 can detect WBC (white blood cell), NEUT (neutronphile), LYMPH (lymphocyte), EO (eosinocyte), BASO (basocyte), and MONO (monocyte) by employing flow cytometry in which a semiconductor laser is used.

The detecting section 513 of the measurement unit 51 can measure reticulocyte (RET) as well. To measure RET, a measurement specimen is prepared by mixing the sample with a reagent for RET measurement, and the prepared measurement specimen is supplied to an optical detector of the detecting section 513 provided to detect WBC/DIFF (five categories of WBC).

The measurement units 52 and 53 are structurally similar to the measurement unit 51 and can measure CBC, DIFF, and RET similarly to the measurement unit 51.

The sample container transport section 515 has a hand portion 515a which can grip the sample container T. The sample container transport section 515 can move the hand portion 515a upward and downward, and also forward and backward (Y direction). The hand portion 515a takes the sample container T housed in the sample rack L and placed at the supply position 35c out of the sample rack L and sets the sample container T in a recess of a sample container setter 515b. The sample container setter 515b is then moved to the suctioning position.

Figure 7:
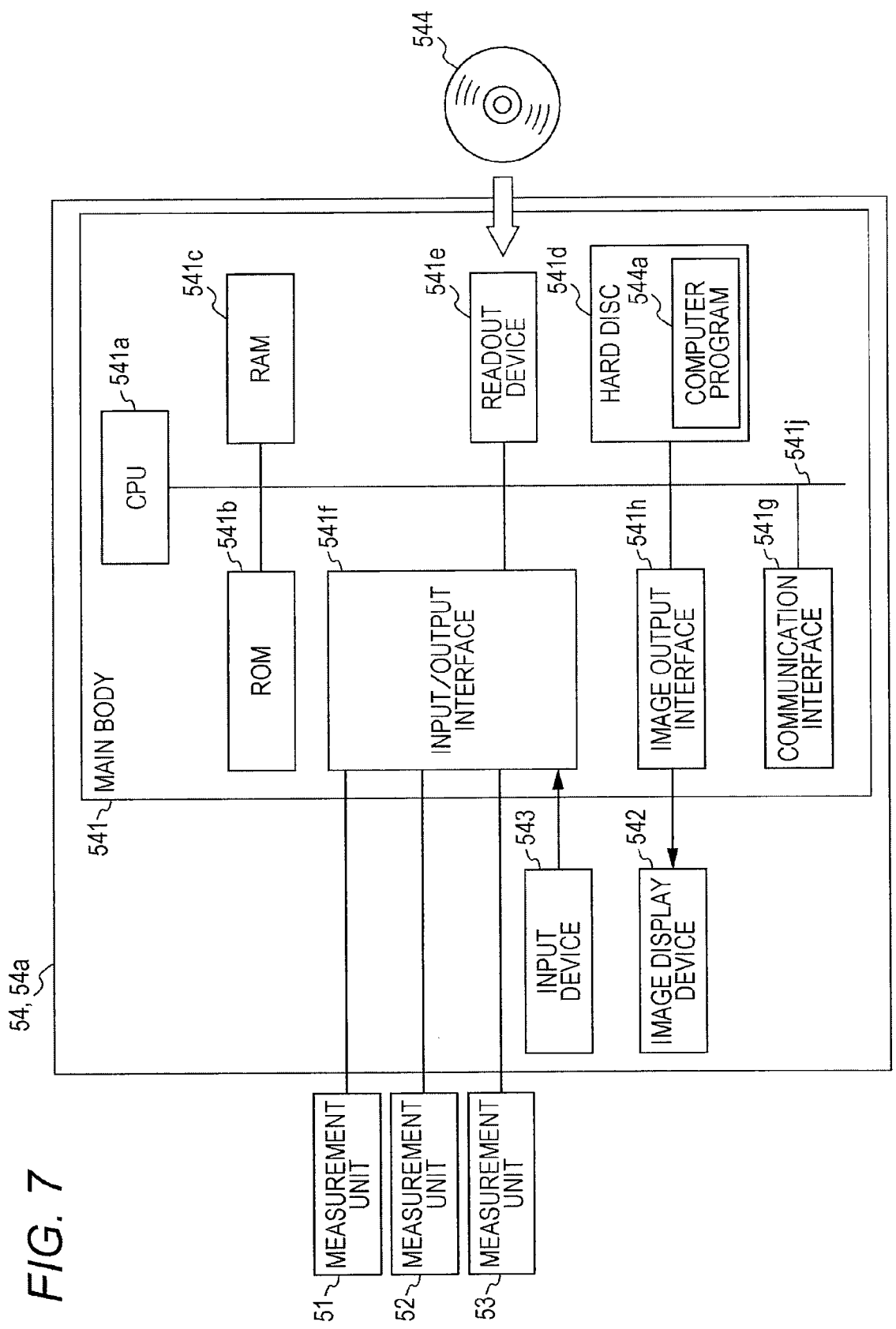
FIG. 7 is a block diagram illustrating a structure of an information processing unit provided in the blood analysis apparatus according to the embodiment.

Hereinafter, a structure of the information processing unit 54 is described. The information processing unit 54 includes a computer. FIG. 7 is a block diagram illustrating the structure of the information processing unit 54. The information processing unit 54 is run by a computer 54a. As illustrated in FIG.

7, the computer 54a has a main body 541, an image display device 542, and an input device 543. The main body 541 has a CPU 541a, a ROM 541b, a RAM 541c, a hard disc 541d, a readout device 541e, an input/output interface 541f, a communication interface 541g, and an image output interface 541h. The CPU 541a, ROM 541b, RAM 541c, hard disc 541d, readout device 541e, input/output interface 541f, communication interface 541g, and image output interface 541h are connected to one another by a bus 541j.

The readout device 541e can read out a computer program 544a which makes the computer function as the information processing unit 54 from a transportable recording medium 544, and install the computer program 544a in the hard disc 541d.

[Structure of Smear Sample Preparing Apparatus 6]

To prepare a smear sample, the smear sample preparing apparatus 6 suctions the blood sample and drops the suctioned blood on a glass slide, spreads the dropped sample on the glass slide very thin, dries the spread sample, and then supplies a staining liquid on the glass slide to stain the blood thereon.

Figure 8:
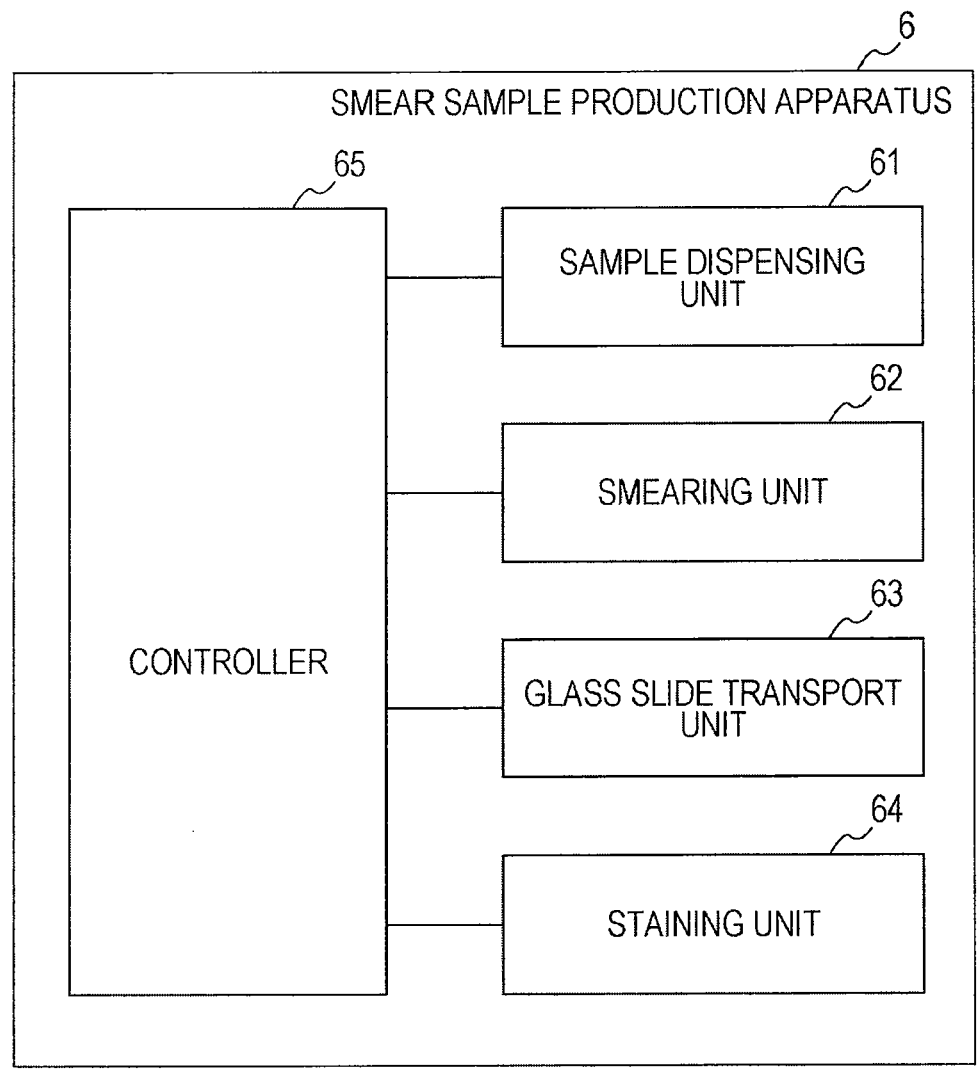
FIG. 8 is a block diagram schematically illustrating a structure of the smear sample preparing apparatus according to the embodiment.

FIG. 8 is a block diagram illustrating a schematic structure of the smear sample preparing apparatus 6. As illustrated in FIG. 8, the smear sample preparing apparatus 6 has a sample dispensing unit 61, a smearing unit 62, a glass slide transport unit 63, a staining unit 64, and a controller 65.

The sample dispensing unit 61 has a suctioning tube (not illustrated in the drawing). The sample dispensing unit 61 penetrates the suctioning tube through the cap portion CP of the sample container T held in the sample rack L transported on the processing line 4M of the sample transport unit 4 to suction the blood sample from the sample container T. The sample dispensing unit 61 drops the suctioned blood sample on the glass slide. The smearing unit 62 smears the blood sample dropped on the glass slide, and dries and prints the dropped blood sample on the glass slide.

The glass slide transport unit 63 is provided to house the glass slide on which the blood sample is smeared by the smearing unit 62 in a cassette not illustrated in the drawing and transports the cassette. The staining unit 64 supplies the staining solution to the glass slide in the cassette transported to a staining position by the glass slide transport unit 63. The controller 65 controls the sample dispensing unit 61, smearing unit 62, glass slide transport unit 63, and staining unit 64 in accordance with a sample preparation guidance obtained from the sample transport apparatus 3 to carry out the smear sample preparation described earlier.

[Structure of System Controller 8]

The system controller 8 including a computer controls the overall operation of the sample processing system 1. The system controller 8 receives the rack number of the sample rack L from the sample loading and collection apparatus 2 and decides a destination of the sample rack L, and then transmits transport instruction data indicating the decided destination to the sample transport apparatus 3.

Figure 9:
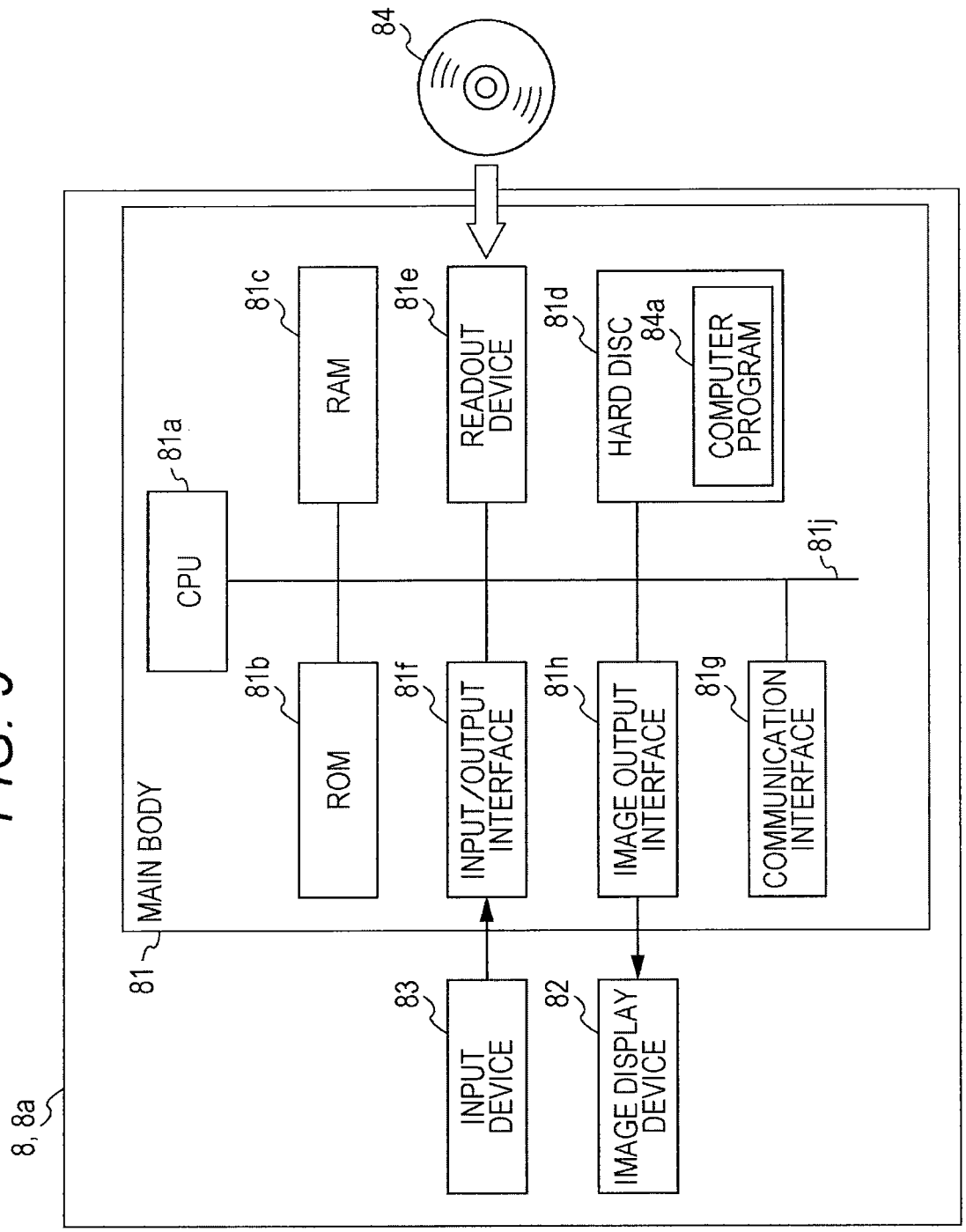
FIG. 9 is a block diagram illustrating a structure of a system controller according to the embodiment.

FIG. 9 is a block diagram illustrating a structure of the system controller 8 according to the present embodiment. The system control device 8 is run by a computer 8a. As illustrated in FIG. 9, the computer 8a has a main body 81, an image display device 82, and an input device 83. The main body 81 has a CPU 81a, a ROM 81b, a RAM 81c, a hard disc 81d, a readout device 81e, an input/output interface 81f, a communication interface 81g, and an image output interface 81h. The CPU 81a, ROM 81b, RAM 81c, hard disc 81d, readout device 81e, input/output interface 81f, communication interface 81g, and image output interface 81h are connected to one another by a bus 81j.

The readout device 81e can read out a computer program 84a which makes the computer function as the system controller 8 from a transportable recording medium 84, and install the computer program 84a in the hard disc 81d.

<Structure of Test Information Management Apparatus 9>

The test information management apparatus 9 is an apparatus which manages information relating to tests performed in a facility, generally called LIS (Laboratory Information System), which is connected not only to the blood cell analysis apparatus 5 but also to a clinical sample testing apparatus. The test information management apparatus 9 receives a measurement order inputted by an operator or transmitted from a device such as an electronic chart system, and stores and manages the received measurement order. Further, the test information management apparatus 9 receives an order request from the system controller 8 and transmits the requested measurement order to the system controller 8, and also receives an analysis result from the blood cell analysis apparatus 5 and stores and manages the received analysis result.

The test information management apparatus 9 including a computer has CPU, ROM, RAM, hard disc, and communication interface. The communication interface is connected to the LAN mentioned earlier and can thereby communicate with the system controller 8 and the information processing unit 54 of the blood cell analysis apparatus 5. The measurement order is stored in the hard disc. The measurement order includes information such as sample ID and sample components to be measured. When the test information management apparatus 9 receives measurement order request data including the sample ID from any other apparatus, the test information management apparatus 9 reads out measurement data relevant to the received sample ID from the hard disc and transmits the data to the apparatus which requested the data. The rest of the structure of the test information management apparatus 9 is similar to the other computers described so far, and will not be any further described.

[Operation of Sample Processing System]

An operation of the sample processing system according to the present embodiment is described below. Below is described a flow of the sample rack transport operation by the sample transport unit 3a. However, the sample transport units 3b and 3c carry out a similar sample rack transport operation.

<Transport Mode Setting Operation>

Figure 10:
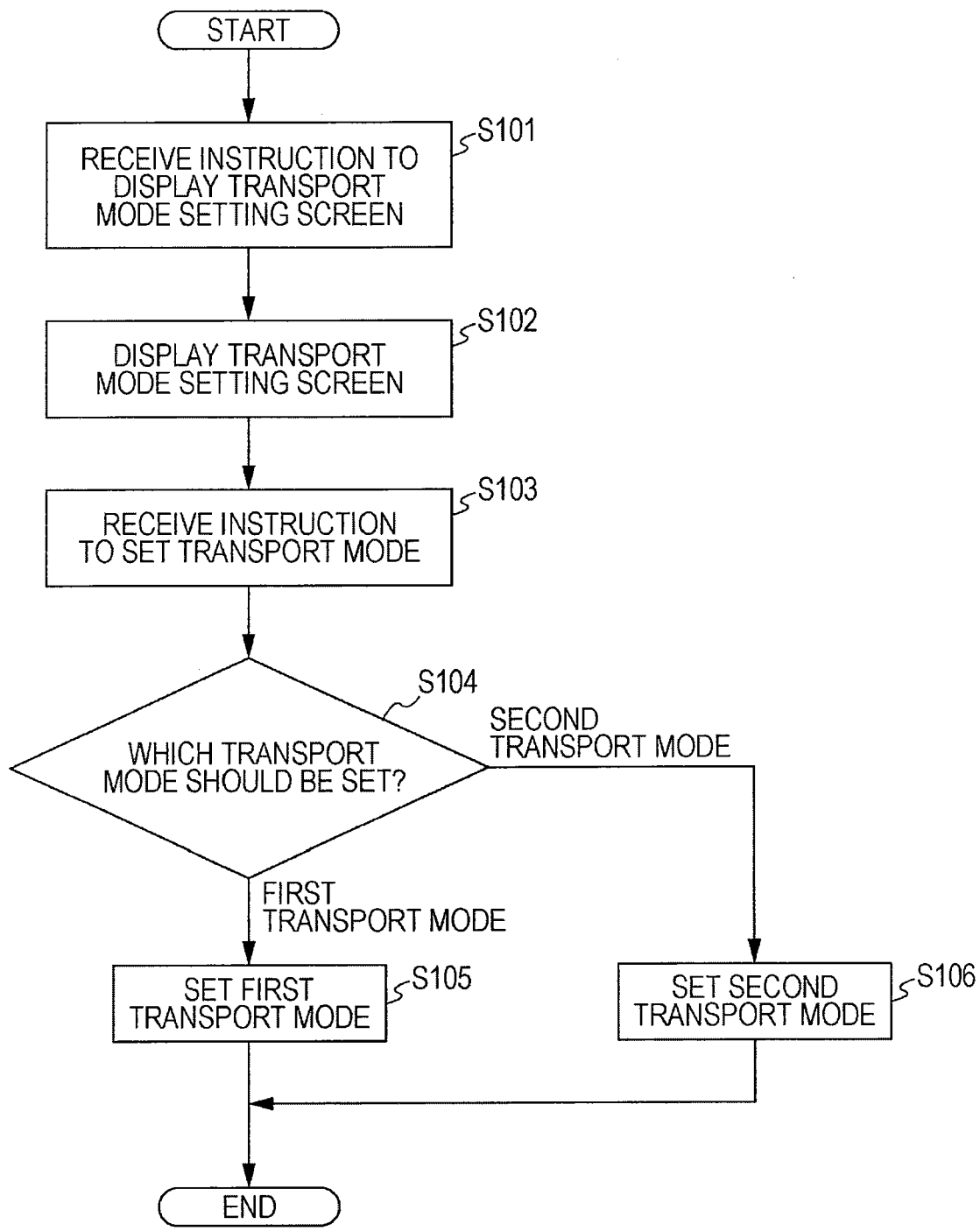
FIG. 10 is a flow chart illustrating processing steps in setting a transport mode carried out by the system controller according to the embodiment.

The system controller 8 executes a transport mode setting process, and the sample processing system 1 accordingly sets the transport mode. FIG. 10 is a flow chart illustrating processing steps for setting the transport mode carried out by the system controller 8. The transport mode is set as initial setting when, for example, the sample processing system 1 is installed in a facility. When an operator or a serviceman sets the transport mode, he or she inputs an instruction to display a transport mode setting screen to the system controller 8 by manipulating the input device 83 of the system controller 8. When the CPU 81a of the system controller 8 receives the instruction to display the transport mode setting screen (Step S101), the CPU 81a displays the transport mode setting screen (not illustrated in the drawing) on the image display device 82 (Step S102). The transport mode setting screen is a screen used to set one of a first transport mode and a second transport mode. An instruction to set the first transport mode or an instruction to set the second transport mode can be inputted to the screen. In the first transport mode, the measurement unit for first test only, more specifically the measurement unit used to perform an initial sample measurement, and the measurement unit for retest only, more specifically the measurement unit used to perform a second sample measurement onwards are selected, and the sample rack is transported so that the first test and the retest are performed by the different measurement units. In the second mode, all of the measurement units can be used for the first test and retest both, and the sample rack is transported so that the measurement unit which first tested the sample can retest the same sample.

Next, the CPU 81a receives the instruction to set the transport mode (Step S103), and determines whether the instructed transport mode is the first transport mode or the second transport mode (Step S104). When it is determined that the instructed transport mode is the first transport mode ("first transport mode" in Step S104), the CPU 81a sets the first transport mode (Step S105). When it is determined that the instructed transport mode is the second transport mode ("second transport mode" in Step S104), the CPU 81a sets the second transport mode (Step S106). To specifically describe the transport mode setting, information indicating the instructed transport mode is stored as a set value in the hard disc 81d. More specifically, information indicating the first transport mode is stored as a set value in the hard disc 81d when it is instructed to set the first transport mode, and information indicating the second transport mode is stored as a set value in the hard disc 81d when it is instructed to set the second transport mode. After the transport mode is thus set, the CPU 81a terminates the processing steps.

<Sample Rack Transport Operation in First Transport Mode>

Next is described a sample rack transport operation carried out by the sample processing system 1 when the first transport mode is set. In the description below, the measurement units 51 and 52 are used for first test only, and the measurement unit 53 is used for retest only.

The sample rack L holding a plurality of sample containers T is loaded in the sample loading unit 1 by an operator. The measurement orders of the respective samples retained in the sample rack L are stored in the test information management apparatus 9. The measurement orders are stored in a measurement order database provided in the hard disc 91d. FIG. 11 is a schematic illustration of measurement orders of pre-measurement samples stored in the test information management apparatus 9. As illustrated in FIG. 11, a measurement order database DB is a table format database. The measurement order database has fields, respectively showing rack ID, holding position in the sample rack L, sample ID, and measurement items which are CBC, DIFF, RET, and SP (smear sample preparation). The measurement order of each sample is registered as a sample record in the measurement order database DB. In the description of the present embodiment, one or both of CBC and DIFF are measurement items as targets to be performed when the sample is first tested, and one or both of RET and SP are measurement items as targets to be performed when the sample is tested again depending on a result of the first test. It is known from the measurement orders of FIG. 11 that all of the samples are tested for the first time. Therefore, information indicating a target to be performed "1" is stored in one or both of cells of CBC and DIFF, while information indicating a non target to be performed "0" is stored in one or both of cells of RET and SP.

When the sample rack L is loaded in the sample loading unit 21 and an instruction to start processing of the sample is inputted by the operator, the sample rack L is transported from the sample loading unit 21 to the pre-processing unit 22 so that the sample ID is read out from the sample barcode label BL of the sample container T and the rack ID is read out from the rack barcode label of the sample rack L by the barcode readout device 22b of the pre-processing unit 22. The sample ID and the rack ID thus read out are transmitted to the test information management apparatus 9 by way of the system controller 8 so that the measurement order relevant thereto is requested. The test information management apparatus 9 reads out the requested measurement order of the sample ID from the hard disc 91d and transmits the measurement order to the system controller 8. The system controller 8 decides which of the measurement units is the transport destination of the sample rack L based on the received measurement order and the current operation conditions of the measurement units 51 and 52 at the time, and transmits an instruction to send the sample rack to the decided destination to the sample transport apparatus 3.

The sample rack L is transported from the pre-processing unit 22 to the sample transport apparatus 3, and then transported by the sample transport unit 3a, 3b to the measurement line 3aM or 3bM of the measurement unit 51 or 52 which is the transport destination. Then, the sample container T is transferred to the sample supply position 35c and fetched into the measurement unit 51 or 52. The system controller 8 supplies the sample ID of each sample held in the transported sample rack L to the information processing unit 54. The information processing unit 54 transmits measurement order request data including the sample ID to the test information management apparatus 9. The test information management apparatus 9 reads out the measurement order relevant to the sample ID included in the measurement order request data from the measurement order database DB, and transmits the measurement order to the information processing unit 54. In the measurement unit 51 or 52, the sample is suctioned from the sample container T and measured based on the measurement order requested for the suctioned sample. After the sample suctioning is completed, the sample container T is discharged from the measurement unit 51 or 52 and returned to the original holding position in the sample rack L. A result of the sample measurement is supplied to the information processing unit 54, and the information processing unit 54 analyzes the measurement result to obtain an analysis result of the sample. The information processing unit 54 transmits the sample analysis result to the test information management apparatus 9. The test information management apparatus 9 which received the analysis result updates the measurement order of the sample relevant to the analysis result with a post-analysis measurement order in the measurement order database DB.

FIG. 12 is a schematic illustration of measurement orders of post-measurement samples stored in the test information management apparatus 9. In the measurement orders illustrated in FIG. 12, the information indicating a non target to be performed "0" is stored in all of CBC, DIFF, RET, and SP because the first test is already completed for all of the samples.

The test information management apparatus 9 processes the received analysis result to decide whether the sample should be retested, and decide a measurement item when the retest is requested. The test information management apparatus 9 registers the decision on whether the retest is necessary and the measurement item in the record of the target sample in the measurement order database DB. FIG. 13 is a schematic illustration of measurement orders of post-analysis samples stored in the test information management apparatus 9. In the measurement orders illustrated in FIG. 13, the information indicating a retesting item "1" is stored in the cells of RET and SP of the measurement order of the sample having a sample ID "P121". The information indicating a non retesting target to be performed "0" is stored in the cells of RET and SP of the measurement order of the sample having a sample ID "P122". In the measurement order of the sample having a sample ID "P129", "1" is stored in the cell of RET, and "0" is stored in the cell of SP. In the measurement order of the sample having a sample ID "P130", "0" is stored in the cell of RET, and "1" is stored in the cell of SP.

The sample containers T retained in the sample rack L are consecutively fetched at the holding position 1 into the measurement unit 51 or 52 so that the samples are measured. When all of the sample containers T are returned from the measurement unit 51 or 52 to their sample rack L, the sample rack L is transferred to the post-analysis rack delivering position 391 of the measurement line 3aM or 3bM by the sample transport unit 3a or 3b, and then pushed into the post-analysis rack holding section 34 from the post-analysis rack delivering position 391 by the rack delivering section 39.

Figure 14:
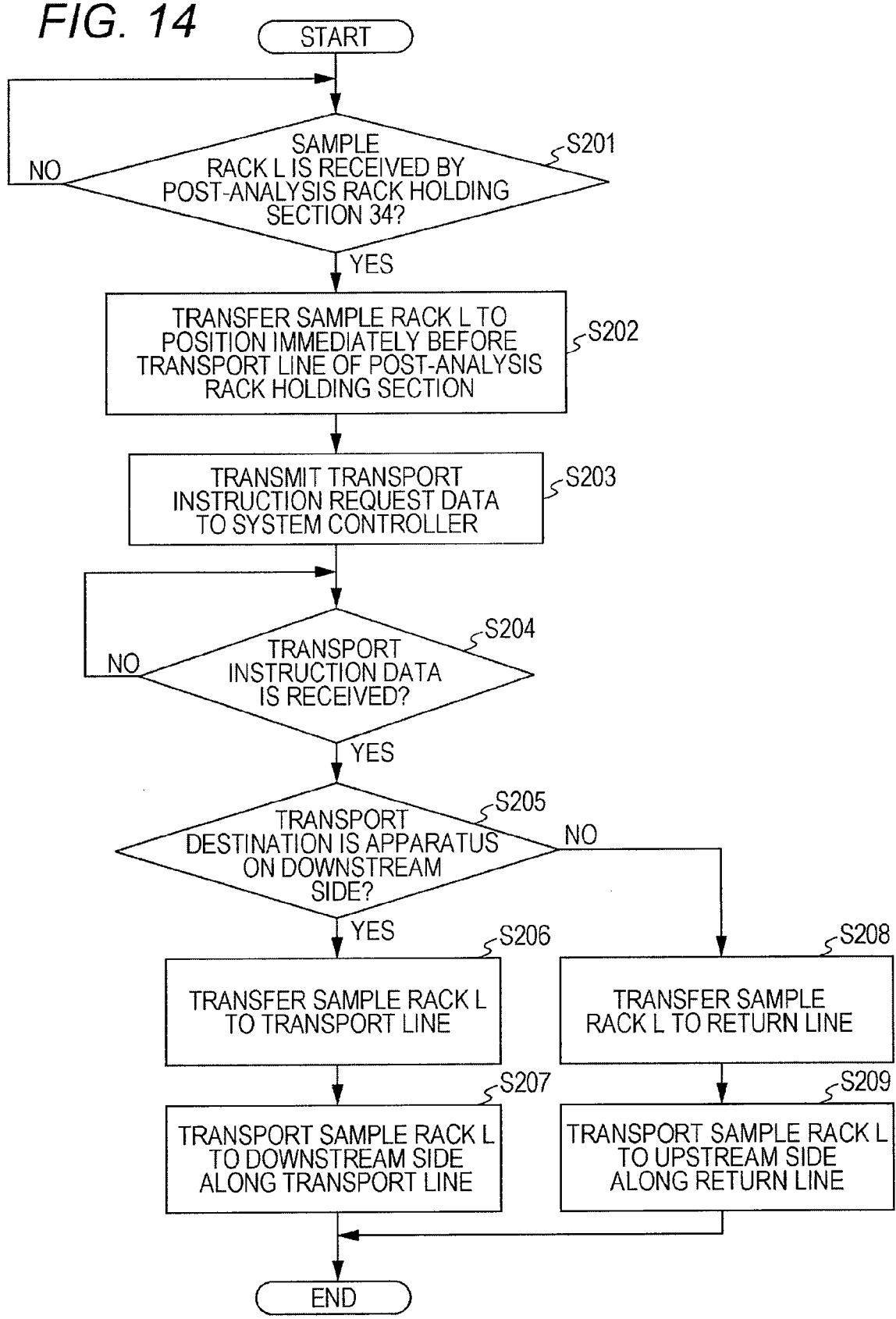
FIG. 14 is a flow chart illustrating transport control processing steps carried out by the sample transport unit in a first transport mode.

FIG. 14 is a flow chart illustrating processing steps for controlling the transport of the sample rack L carried out by the sample transport unit in the first transport mode. The controller 32 determines whether the post-analysis rack holding section 34 receives the sample rack L from the measurement line 3aM or 3bM (Step S201). Whether the sample rack L is received is determined by monitoring an output signal of the rack sensor 372. When the receipt of the sample rack L in the post-analysis rack holding section 34 is not detected (NO in Step S201), the controller 32 repeatedly carries out the processing step of S201 until the receipt of the sample rack L is detected. When the receipt of the sample rack L in the post-analysis rack holding section 34 is detected (YES in Step S201), the controller 32 moves the rack senders 34b to transfer the sample rack L to a position immediately before the skipping line 3aF or 3bF in the post-analysis rack holding section 34 (Step S202) and stops the sample rack L there. Then, the controller 32 transmits transport instruction request data including the sample IDs of the samples contained in the sample rack L to the system controller 8 (Step S203).

Figure 15:
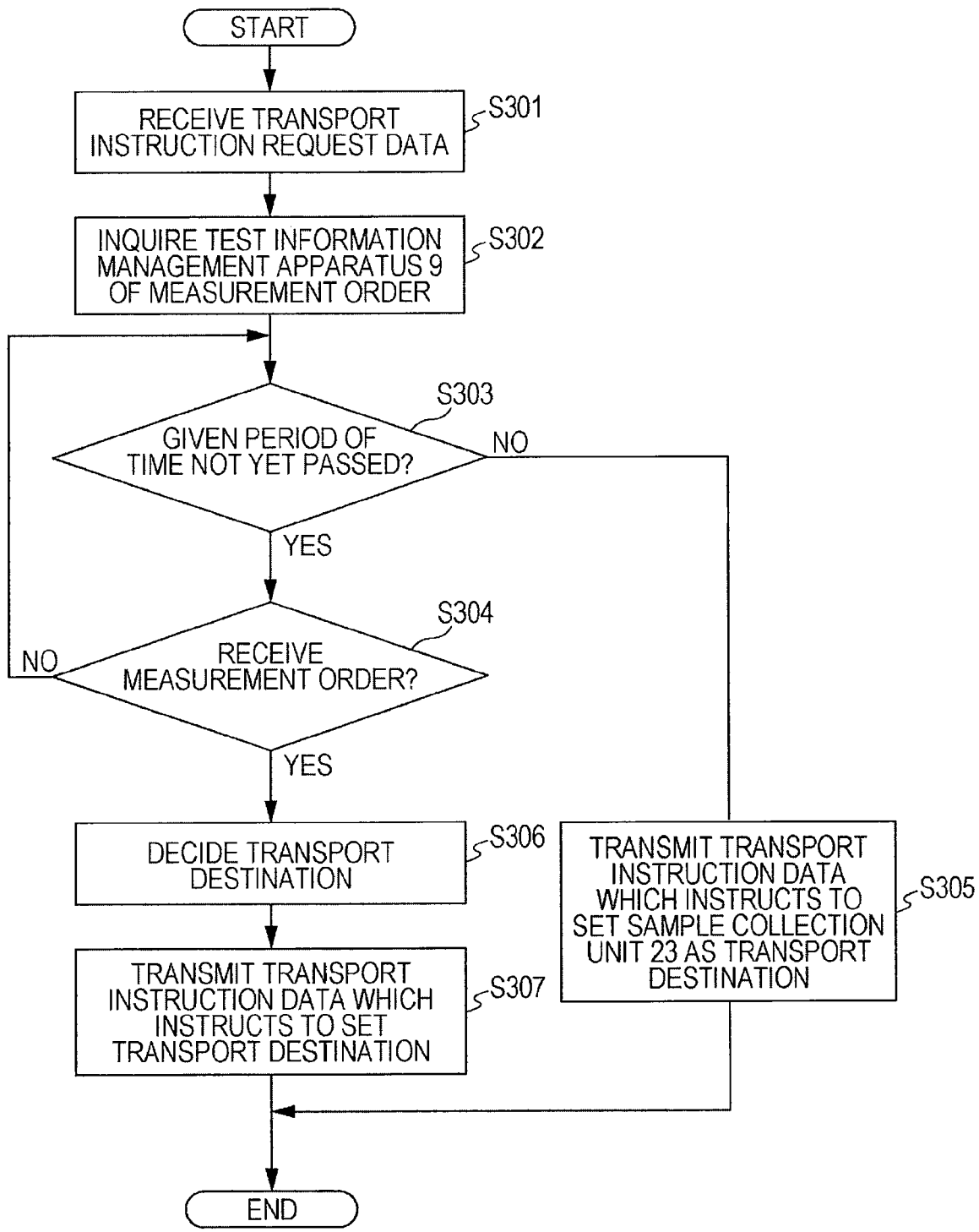
FIG. 15 is a flow chart illustrating transport instruction processing steps carried out by the system controller in the first transport mode.

FIG. 15 is a flow chart illustrating processing steps for instructing the transport of the sample rack L carried out by the system controller 8 in the first transport mode. When the system controller 8 receives the transport instruction request data from the sample transport apparatus 3 (Step S301), the CPU 81a inquires the test information management apparatus 9 of the measurement order using the sample ID included in the transport instruction request data (Step S302). The test information management apparatus 9 reads out the measurement order corresponding to the sample ID included in the inquired data from the measurement order database DB, and transmits the measurement order to the system controller 8. The measurement order transmitted then relates to the sample for which the first test is done and the analysis result is already processed. Therefore, the measurement order includes the determination result on whether the retest is necessary illustrated in FIG. 13.

The CPU 81a determines whether a given period of time (120 seconds) passed after the inquiry of the measurement order was made (Step S303). In the case where the given period of time has not yet passed (YES in Step S303), the CPU 81a determines whether the measurement orders of all of the samples contained in the sample rack L are received (Step S304). In the case where there is any measurement order not yet received (NO in Step S304), the CPU 81a returns the processing to the processing step of S303.

In the case where in Step S303, it is determined that the given period of time has passed (NO in Step S303) since the inquiry of the determination order, the CPU 81a transmits the transport instruction data indicating that the transport destination of the sample rack L is the sample collection unit 23 to the sample transport apparatus 3 (Step S305), and terminates the processing steps.

When in Step S304, the measurement orders of all of the samples contained in the sample rack L on standby is received in the post-analysis rack holding section 34 (YES in Step S304), the CPU 81a decides the transport destination of the sample rack L based on the received measurement orders (Step S306). In the case where any of the measurement orders includes RET or SP as an item to be retested during the processing step of S304, the measurement unit 53 or the smear sample preparing apparatus 6 which can process REP and SP is decided as the transport destination. When the measurement orders illustrated in FIG. 13 are obtained, for example, it is necessary to measure RET (reprocess) of the samples having sample IDs P121 and P129, and it is necessary to prepare smear samples (reprocess) of the samples having sample IDs P121 and P130. Accordingly, RET is measured in the measurement unit 53 for retest only, and the smear samples are prepared by the smear sample preparing apparatus 6 for retest only. Therefore, the sample rack L should be transported to the measurement unit 53 and the smear sample preparing apparatus 6 both. The CPU 81a, therefore, selects the measurement unit 53 positioned on the upstream side of the transport direction as the transport destination of the sample rack L from the two destination apparatuses, measurement unit 53 and smear sample preparing apparatus 6. In the case where none of the received measurement orders includes any item other than RET as a retesting item in Step S306, the measurement unit 53 is similarly decided as the transport destination. In the case where none of the received measurement orders includes any item other than SP as a retesting item, the smear sample preparing apparatus 6 is decided as the transport destination. In the case where none of the received measurement orders includes RET or SP as a retesting item, the sample collection unit 23 is decided as the transport destination.

After the processing step of S306, the CPU 81a transmits the transport instruction data indicating the transport destination thus decided (S307), and terminates the processing steps.

Referring to FIG. 14, the controller 32 which implemented the processing step of S203 waits for the transport instruction data to be received (NO in Step S204). When the controller 32 receives the transport instruction data transmitted from the system controller 8 (YES in Step S204), the controller 32 determines whether the transport destination instructed by the transport instruction data is the apparatus on the downstream side of the transport direction, more specifically, whether the transport destination is the measurement unit 53 or the smear sample preparing apparatus 6 (Step S205). In the case where the transport destination instructed by the transport instruction data is the apparatus on the downstream side of the transport direction (YES in Step S205), the controller 32 moves the rack senders 34b to transfer the sample rack L to the skipping line 3aF or 3bF (Step S206), and then drives the belt conveyer 321 to transport the sample rack L to the sample transport unit on the downstream side (Step S207). Then, the controller 32 ends the processing steps. After that, the sample rack L is transported by the sample transport unit on the downstream side to the transport destination, which is the measurement unit 53 or the smear sample preparing apparatus 6, so that the samples are retested.

In the case where in Step S205, it is determined that the transport destination instructed by the transport instruction data is not the apparatus on the downstream side of the transport direction, in other words, the transport destination is the sample collection unit 23 (NO in Step S205), the controller 32 moves the rack senders 34b to transfer the sample rack L to the return line 3aR or 3bR (Step S208), and then drives the belt conveyer 331 to transport the sample rack L to the sample transport unit or the sample collection apparatus 2 on the upstream side (Step S209). Then, the controller 32 ends the processing steps. The sample rack L is thereafter transported by the collection line 223, 217, 237 to be finally collected by the sample collection unit 23.

After RET is retested by the measurement unit 53, an analysis result of the retest is transmitted to the test information management apparatus 9 to decide whether retesting is necessary and any items to be retested in a manner similar to the first test. In the case where the smear sample preparation is determined as necessary for the target sample, "1" is stored in the cell of SP of the measurement order of the target sample in the measurement order database DB. In this case, similarly to the first test, the sample rack L is retained in the post-analysis rack holding section 34 of the sample transport unit 3c, and the system controller 8 inquires the test information management apparatus 9 of the measurement order. In the case where SP is set as a retesting item in the measurement order obtained by the inquiry, the smear sample preparing apparatus 6 is decided as the transport destination, and the sample rack L is similarly transported to the smear sample preparing apparatus 6. When the sample rack L is transported to the smear sample preparing apparatus 6, the sample is suctioned to prepare the smear sample, and the sample rack L is thereafter transported by the return line 4R, 3cR, 3bR, 3aR to the sample collection unit 23. In the case where SP is not set as a retesting item in the measurement order obtained by the inquiry, the sample collection unit 23 is decided as the transport destination, and the sample rack L is transported to the sample collection unit 23.

<Sample Rack Transport Operation in Second Transport Mode>

Next is described a sample rack transport operation carried out by the sample processing system 1 when the second transport mode is set. In the case where the measurement unit which first tested the sample can remeasure any item of the sample to be retested in the second transport mode, the sample is transported to the measurement unit which first tested the sample. In the case where the measurement unit which first tested the sample is unable to remeasure any item of the sample to be retested, the sample is transported to the measurement units other than the measurement unit which first tested the sample (or smear sample preparing apparatus).

Figure 16:
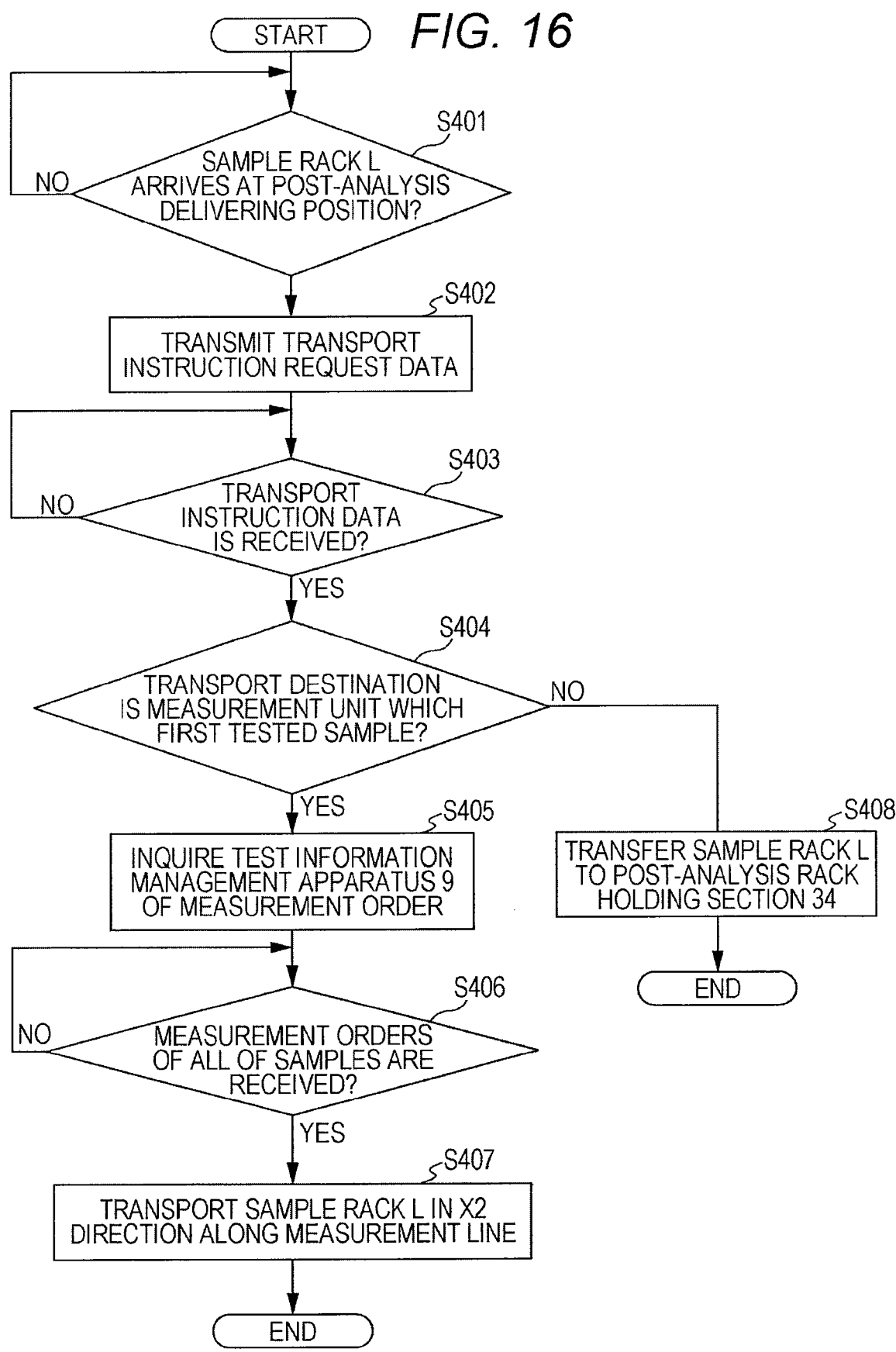
FIG. 16 is a flow chart illustrating transport control processing steps carried out by the information processing unit in a second transport mode.

FIG. 16 is a flow chart illustrating processing steps for controlling the transport of the sample rack L carried out by the CPU 541a of the information processing unit 54 in the second transport mode. After all of the sample containers T are returned to the sample rack L from the measurement unit which first tested the sample, the CPU 541a determines whether the sample rack L arrives at the post-analysis rack delivering position 391 (Step S401). When determined that the sample rack L arrived at the position, the CPU 541a stops the sample rack there, and transmits the transport instruction request data including the sample IDs of the samples retained in the sample rack L to the system controller 8 by way of the sample transport apparatus 3 (Step S402).

The system controller 8 executes processing steps of the transport instruction of the sample rack L in the second transport mode. According to the transport instruction processing steps in the second transport mode, in the case where any of the measurement orders includes RET or SP as an item to be retested when the transport destination of the sample rack L is decided, the measurement unit 51, 52, or 53 which first tested the sample or the smear sample preparing apparatus 6 capable of carrying out SP is decided as the transport destination. In the case where, for example, the first test is carried out by the measurement unit 51 and the measurement orders illustrated in FIG. 13 are thereby obtained, it is necessary that the measurement unit 51 which first tested the sample measure RET of the samples P121 and P129, and the smear sample preparing apparatus 6 prepare the smear samples of the samples P121 and P130. The CPU 81a selects the measurement unit 51 positioned on the upstream side of the transport direction from the measurement unit 51 and the smear sample preparing apparatus 6 as the transport destination of the sample rack L. In the case where none of the received measurement orders includes any item other than RET as an item to be retested, the measurement unit 51 is similarly decided as the transport destination. In the case where none of the received measurement orders includes any item other than SP as an item to be retested, the smear sample preparing apparatus 6 is decided as the transport destination. In the case where none of the received measurement orders includes RET or SP as an item to be retested, the sample collection unit 23 is decided as the transport destination.

The transport instruction processing steps in the second transport mode are similar to the transport instruction processing steps in the first transport mode other than the processing steps for deciding the transport destination described so far. Therefore, description of the rest of the processing steps is omitted.

The transport instruction data transmitted from the system controller 8 is received by the sample transport apparatus 3 and then transmitted from the sample transport apparatus 3 to the information processing unit 54. Referring to FIG. 16, the controller 541a which implemented the processing step of S402 waits for the transport instruction data to be received (NO in Step S403). When the controller 541a receives the transport instruction data (YES in Step S403), the controller 541a determines whether the transport destination instructed by the transport instruction data is the measurement unit 51, 52, or 53 which first tested the samples held in the sample rack L on standby at the post-analysis rack delivering position (Step S404). In the case where the transport destination is the measurement unit 51, 52, or 53 which first tested the samples retained in the sample rack L on standby at the post-analysis rack delivering position (YES in Step S404), the CPU 541a transmits the measurement order request data including the sample IDs of the samples to the test information management apparatus 9 and makes an inquiry of the measurement orders of these samples (Step S405). The test information management apparatus 9 reads out the measurement orders corresponding to the sample IDs from the hard disc 91d and transmits the measurement orders to the information processing unit 54.

Next, the CPU 541a determines whether the measurement orders of all of the samples held in the sample rack L are already received (Step S406). In the case where there is any measurement order not yet received (NO in Step S406), the CPU 541a returns the processing to the processing step of S406. When determined that the measurement orders of all of the samples held in the sample rack L were received (YES in Step S406), the CPU 541a drives the belt conveyer 353 in the opposite direction to transport the sample rack L in the direction of X2 (rightward) along the measurement line 3aM, 3bM, or 3cM (Step S407). Thereafter, to retest all of the samples which need to be retested, the sample containers T are fetched, the samples contained therein are suctioned, measured and analyzed (retested), and the sample containers T are thereafter discharged. Further, the analysis result of retested sample is transmitted to the test information management apparatus 9, and the measurement order of the sample relevant to the analysis result is updated in the measurement order database DB of the test information management apparatus 9. At the time, "0" is registered in the cells of RET of retested P121 and P129. Therefore, any sample once measured by the measurement unit 51, 52, or 53 is never measured again by the measurement unit 51, 52, or 53 but is used for the preparation of the smear sample or collected by the sample collection unit 23.

In the case where in Step 404, it is determined that the instructed transport destination is not the measurement unit 51, 52, or 53 which first tested the samples held in the sample rack L on standby at the post-analysis rack delivering position but is the apparatus on the downstream side of the transport direction (smear sample preparing apparatus 6) or the sample collection unit 23 (NO in Step S404), the CPU 541a drives the rack delivering section 39 to transfer the sample rack L on standby at the post-analysis rack delivering position 391 to the post-analysis rack holding section 34 (Step S408).

After that, the same transport control processing steps as in Steps S201 to S209 are carried out by the controller 32. In the case where the transport destination is the apparatus on the downstream side of the transport direction (smear sample preparing apparatus 6), upon the sample rack being transported to the post-analysis rack holding section 34, the sample transport unit 3a, 3b, or 3c transfers the sample rack L to the skipping line 3aF, 3bF, or 3cF using the rack senders 34b, and then drives the belt conveyer 321 to transport the sample rack to the sample transport unit 4 on the downstream side. Then, the sample rack L is transported to the smear sample preparing apparatus 6 decided as the transport destination by the sample transport unit 4 so that the smear samples of the samples are prepared by the smear sample preparing apparatus 6. After all of the samples, for which the preparation of their smear samples is requested, are suctioned so that their smear samples are prepared, the sample rack L is transported by the return line 4R, 3cR, 3bR, 3aR and then sent to the sample collection unit 23.

In the case where the transport destination is the sample collection unit 23, upon the sample sack L being transported to the post-analysis rack holding section 34, the sample transport unit 3a, 3b, or 3c transfers the sample rack L to the return line 3aR, 3bR, or 3cR using the rack senders 34b, and then drives the belt conveyer 331 to transport the sample rack to the sample loading and collection apparatus 2. The sample rack L is thereafter transported by the collection line 223, 217, 237 to be finally collected by the sample collection unit 23.

As described earlier, the sample loading unit 21 and the sample collection unit 23 are provided on the same side apart from measurement units 51, 52, and 53 and the smear sample preparing apparatus 6. Therefore, an operator (user) can easily load and collect the sample in one place.

After the first test is conducted by the measurement unit 51, 52, or 53, the sample rack L containing any samples which need to be retested is transported to one of the measurement unit 51, 52, or 53 or the smear sample preparing apparatus 6 along the supply line 3aS, 3bS, 3cS, or 4S. When the first transport mode is set, the sample rack L holding any samples which need to be retested subsequent to the first test conducted by the measurement unit 51 or 52 is transported in the direction of X1 along the skipping line 3aF, 3bF, 3cF, or transport line 4F so that the sample is retested by the measurement unit 53 or the smear sample preparing apparatus 6 for retest only. When the second transport mode is set, the sample rack L holding any samples which need to be retested by the measurement unit 51, 52, or 53 subsequent to the first test conducted by the measurement unit 51, 52, or 53 is transported in the direction of X2 along the measurement line 3aM, 3bM, or 3cM so that the sample is retested (remeasured) by the measurement unit 51, 52, or 53 which first tested the sample. When the second transport mode is set, the sample rack L holding any samples for which the smear sample preparation requested subsequent to the first test conducted by the measurement unit 51, 52, or 53 is transported in the direction of X1 along the skipping line 3aF, 3bF, or 3cF, or transport line 4F so that the sample is processed to be retested by the smear sample preparing apparatus 6. The sample rack L holding any samples which need to be retested is immediately transported for retesting to one of the measurement units 51, 52, and 53 and the smear sample preparing apparatus 6 to retest the samples. Thus, the sample can be very efficiently retested (reprocessed).

The sample rack L holding only the samples which need not be retested subsequent to the first test conducted by the measurement unit 51, 52, or 53 does not pass through the terminal point 3E of the supply line 3aS, 3bS, 3cS, or 4S (first transport line) but passes through the rack transport position 3T by way of the post-analysis rack holding section 34 of the sample transport unit 3a, 3b, 3c and then transferred to the return line 3aR, 3bR, 3cR. Thus, the sample rack L can be speedily collected.

[Another Embodiment]

In the embodiment described so far, the supply lines 3aS, 3bS, 3cS, and 4S respectively have the measurement lines 3aM, 3bM, and 3cM, and processing line 4M, skipping lines 3aF, 3bF, and 3cF, transport line 4F, pre-analysis rack holding sections 33 and 43, and post-analysis rack holding sections 34 and 44. However, the present invention is not necessarily limited thereto. Another possible structure is to provide a supply line linearly extending through the sample transport units, and to provide sample supply positions at which the sample is supplied to the measurement units 51, 52, and 53 and the smear sample preparing apparatus 6 at intermediate positions on the supply line. In the suggested structure, a passage which connects an intermediate position of the supply line to intermediate positions on the return lines 3aR, 3bR, 3cR and 4R is provided so that any samples which need not be retested alone are transferred to the intermediate position of the return line 3aR, 3bR, 3cR, or 4R and further in the direction of X2 along the return line 3aR, 3bR, 3cR, or 4R to be finally collected by the sample collection unit 23.

The measurement unit 51, 52, or 53 may directly suction the sample from the sample container T kept in the sample rack L on the measurement line 3aM, 3bM, or 3cM.

In the embodiment described so far, the sample transport apparatus 3 includes the sample transport units 3a, 3b, 3c, and 4 independent from one another. However, the present invention is not necessarily limited thereto. A sample transport apparatus formed as an inseparable single component may be provided on the front side of the measurement units 51, 52, and 53, and the smear sample preparing apparatus 6 to transport the sample rack L to the measurement units 51, 52, and 53, and the smear sample preparing apparatus 6.

In the embodiment described so far, all of the measurement units 51, 52, and 53 can measure the same components (CBC, DIFF, RET), however, the present invention is not necessarily limited thereto. For example, the measurement units 51 and 52 can measure CBC and DIFF of the sample but cannot measure RET of the sample, and the measurement unit 53 can measure all of CBC, DIFF, and RET. When the second transport mode is set in addition to the first transport mode, any sample including RET as a target item to be retested is transported to the measurement unit 53 after the first test is over by the skipping line 3aF, 3bF, 3cF, and then retested in the measurement unit 53.

In the embodiment described so far, the sample processing system 1 has the blood cell analysis apparatus 5 which discriminates the blood cells included in the sample according to their types and counts the different types of blood cells respectively. However, the structure of the sample processing system 1 is not limited thereto. The sample processing apparatus may be equipped with any sample analysis apparatus other than the blood cell analysis apparatus, such as immunoassay apparatus, blood coagulation measurement apparatus, biochemical analysis apparatus, or urine analysis apparatus, wherein a sample such as blood or urine is transported to a measurement unit of the sample analysis apparatus.

When the second transport mode is set in the embodiment described so far, the sample rack L is left on standby at the post-analysis rack delivering position 391 until the determination is made on whether retesting is necessary. Then, when retesting is requested, the sample rack L is transported in the direction of X2 along the measurement line 3aM or 3bM to be supplied to the measurement unit 51 or 52 which first tested the sample. However, the present invention is not necessarily limited thereto. For example, the sample rack L is left on standby in the post-analysis rack holding section 34 until the determination is made on whether retesting is necessary when the second mode is set. When retesting is requested, the sample rack L is transported in the direction of Y1 by the rack senders 34b and then in the direction of X2 along the measurement line 3aM or 3bM so that the sample rack L is finally supplied to the measurement unit 51 or 52 which first tested the sample. In that case, when it is determined that retesting is unnecessary for the samples retained in the sample rack L on standby in the post-analysis rack holding section 34, the sample rack L is transferred in the direction of Y2 to the return line 3aR or 3bR by the rack senders 34b, transported in the direction of X2 along the return line 3aR or 3bR, and then collected by the sample collection unit 23.

In the embodiment described so far, the blood cell analysis apparatus 5 has the three measurement units 51, 52, and 53, and information processing unit 54. However, the structure of the blood cell analysis apparatus 5 is not limited thereto. Either a single or a plurality of measurement units may be provided, and the measurement unit and the information processing unit may be integrally formed. It is not necessary that the information processing unit 54 control the mechanisms of the measurement units 51, 52, and 53. Each of the measurement units may include a controller having a CPU and a memory, wherein the controller controls the measurement unit, and the information processing unit processes measurement data obtained by the measurement unit to generate a sample analysis result.

In the embodiment described so far, the single computer 8a, 80a is solely responsible for all of the processing steps of the computer program 84a, 840a. However, the present invention is not limited thereto. A distributed system may be used, wherein processing steps similar to those of the computer program 84a, 840a are carried out by a plurality of devices (computers) in a distributed manner.

In the embodiment described so far, the sample collection unit 23, sample loading unit 21, pre-processing unit 22, and sample transport apparatus 3 are linearly aligned in the mentioned order from the upstream side of the sample rack transport direction. However, the present invention is not necessarily limited thereto. For example, the sample collection unit 23 may be interposed between the sample loading unit 21 and the pre-processing unit 22. Accordingly, the sample loading unit 21, sample collection unit 23, pre-processing unit 22, and sample transport apparatus 3 are linearly aligned in the mentioned order from the upstream side of the sample rack transport direction.

What is claimed is:
1. A sample processing apparatus comprising:
a plurality of sample processing units arranged along a transporting route, including a first sample processing unit and a second sample processing unit positioned downstream of the first sample processing unit along the transporting route, both first and second sample processing units configured to test a sample held in a rack and issue a test result on the sample;
a sample loading unit located upstream of the plurality of sample processing units and configured to feed pre-tested racks for testing at some of the plurality of sample processing units;
a collecting unit located upstream of the plurality of sample processing units and configured to receive post-tested racks from some of the plurality of sample processing units;
a transport apparatus formed with a plurality of transporting units connected in series along the transporting route to each serve one of the sample processing units, the plurality of transporting units being operable to collectively transport a respective pre-tested rack in a first direction along the transporting route from the sample loading unit to one of the plurality of sample processing units and collectively transport a respective post-tested rack in a second direction along the transporting route from one of the plurality of sample processing units to the collecting unit, a respective at least some of the plurality of transporting units comprising:
a measurement line separated at a distance from the transporting route and having terminal ends disconnected operably and physically from the measurement lines of adjacent transporting units, the measurement line being configured to transport a rack in the first direction separately from the transporting route to supply a sample in the rack to the corresponding sample processing unit;
a skipping line forming a part of the transporting route and having connecting ends operably connected to the skipping lines of the adjacent transporting units, the skipping line being configured to receive a rack from an adjacent upstream transporting unit and transport the received rack in the first direction along the transporting route to an adjacent downstream transporting unit;
a rack delivering section configured to deliver a rack from the skipping line of the corresponding sample processing unit to the measurement line of the corresponding sample processing unit;
a return line forming the part of the transporting route along with the skipping line of the corresponding sample processing unit and having connecting ends operably connected to the return lines of the adjacent transporting units, the return line being configured to receive a rack from the adjacent downstream transporting unit and transport the received rack in the second direction along the transporting route to the adjacent upstream transporting unit; and
a post-analysis rack holding section laid across from the measurement line of the corresponding sample processing unit through the skipping line of the corresponding sample processing unit, and configured to move a rack from the measurement line of the corresponding sample processing unit to one of the skipping line and the return line of the corresponding sample unit, the post-analysis rack holding section being dimensioned to accommodate more than one rack therein, and a controller comprising a memory that stores programs executable by the controller to:

operate the post-analysis rack holding section of the first sample processing unit to hold a post-tested rack comprising samples tested by the first sample processing unit at a position in the post-analysis rack holding section of the first sample processing unit between the measurement line of the first sample processing unit and the transporting route going through the first sample processing unit until the controller analyzes a measurement order for the samples in the post-tested rack and determines from the measurement order where to transport the post-tested rack;

upon a determination by the controller that the measurement order requests one of the samples in the post-tested rack to be retested, operate the post-analysis rack holding section of the first sample processing unit to move the post-tested rack from the post-analysis rack holding section to the skipping line of the first sample processing unit to transport the post-tested rack to the second sample processing unit in the first direction along the transporting route; and upon a determination by the controller that the measurement order request none of the samples in the post-tested rack to be retested, operate the post-analysis rack holding section of the first sample processing unit to move the post-tested rack from the post-analysis rack holding section to the return line of the first sample processing unit to transport the post-tested rack back to the collecting unit in the second direction along the transporting route.

2. The sample processing apparatus according to claim 1, wherein the post-analysis rack holding section is configured to move the post-tested rack between the measurement line and the return line of the first sample processing unit across the skipping line of the first sample processing unit.

3. The sample processing apparatus according to claim 1, wherein the post-analysis rack holding section comprises a pusher to push the post-tested rack to the return line of the first sample processing unit.

4. The sample processing apparatus according to claim 1, wherein the controller is further programmed to request the measurement order and operate the post-analysis rack holding section of the first sample processing unit to hold the post-tested rack at the position in the post-analysis rack holding section until the controller receives the measurement order.

5. The sample processing apparatus according to claim 4, wherein the controller is programmed to determine where to transport the post-tested rack held in the post-analysis rack holding section, according to the received measurement order.

6. The sample processing apparatus according to claim 4, wherein the controller is further programmed to operate the post-analysis rack holding section of the first sample processing unit to move the post-tested rack to the return line of the first sample processing unit to transport the post-tested rack back to the collecting unit when it does not receive the measurement order within a predetermined time.

7. The sample processing apparatus according to claim 1, wherein the processor is further programmed to operate the post-analysis rack holding section of the first sample processing unit to move the post-tested rack from the post-analysis rack holding section to the skipping line of the first sample processing unit to transport the post-tested rack in the first direction along the transporting route to the second sample processing unit, when the post-tested rack contains a sample which requires a test of a type to be performed which is not performable by the first sample processing unit but performable by the second sample processing unit.

8. The sample processing apparatus according to claim 1, wherein the post-analysis rack holding section is laid between the measurement line and the skipping line.

9. The sample processing apparatus according to claim 1, wherein the plurality of sample processing units comprise a sample smearing unit configured to prepare a smear sample of a sample to be retested.

10. A sample processing apparatus, comprising:

a plurality of sample processing units arranged along a transporting route, including a first sample processing unit and a second sample processing unit, positioned downstream of the sample processing unit along the transporting route, both configured to test a sample held in a rack and issue a test result on the sample;

a sample loading unit located upstream of the plurality of sample processing units and configured to feed pre-tested racks for testing at the plurality of sample processing units;

a collecting unit located upstream of the plurality of sample processing units and configured to receive post-tested racks from the plurality of sample processing units;

a transport apparatus formed with a plurality of transporting units connected in series along the transporting route to serve the plurality of sample processing units, respectively, the plurality of transporting units being operable to collectively transport a respective pre-tested rack in a first direction along the transporting route from the sample loading unit to one of the plurality of sample processing units and collectively transport a respective post-tested rack in a second direction along the transporting route from one of the sample processing units to the collecting unit, a respective at least some of the plurality of transporting units comprising:

a measurement line separated at a distance from the transporting route and having terminal ends disconnected both operably and physically from the measurement lines of adjacent transporting units, the measurement line being configured to transport a rack in the first direction separately from the transporting route to supply a sample in the rack to the corresponding sample processing unit;

a skipping line forming a part of the transporting route and having connecting ends operably connected to the skipping lines of the adjacent transporting units, skipping line being configured to receive a rack from an adjacent upstream transporting unit and transport the received rack in the first direction along the transporting route to an adjacent downstream transporting unit;

a rack delivering section configured to deliver a rack from the skipping line of the corresponding sample processing unit to the measurement line of the corresponding sample processing unit;

a return line forming the part of the transporting route along with the skipping line of the corresponding sample processing unit and having connecting ends operably connected to the return lines of the adjacent transporting units, the return line being configured to receive a rack from the adjacent downstream transporting unit and transport the received rack in the second direction along the transporting route to the adjacent upstream transporting unit; and a post-analysis rack holding section laid across from the measurement line of the corresponding sample processing unit through the skipping line of the corresponding sample processing unit, and configured to move a rack from the measurement line of the corresponding sample processing unit to one of the skipping line and the return line of the corresponding sample unit, the post-analysis rack holding section being dimensioned to accommodate more than one rack therein, and a controller comprising a memory that stores programs executable by the controller to:

operate the post-analysis rack holding section of the first sample processing unit to hold a post-tested rack comprising samples tested by the first sample processing unit at a position in the post-analysis rack holding section of the first sample processing unit between the measurement line of the first sample processing unit and the transporting route going through the first sample processing unit until the controller receives a measurement order for the samples in the post-tested rack and determines from the received measurement order where to transport the post-tested rack;

upon a determination by the controller that the received measurement order requests one of the samples in the post-tested rack to be retested, operate the post-analysis rack holding section of the first sample processing unit to move the post-tested rack from the post-analysis rack holding section to the skipping line of the first sample processing unit to transport the post-tested rack to the second sample processing unit in the first direction along the transporting route, and upon a determination by the controller that the received measurement order requests none of the samples to be retested, operate the post-analysis rack holding section of the first sample processing unit to move the post-tested rack from the post-analysis rack holding section to the return line of the first sample processing unit to transport the post-tested rack back to the collecting unit in the second direction along the transporting route, wherein the sample processing apparatus further comprises an information management apparatus configured to:

receive test results of the samples in the post-tested rack from the first sample processing unit;

determine, based on an analysis of the test results, whether or not retesting is necessary on any of the samples held in the post-tested rack; and prepare the measurement order, based on a determination as to whether or not retesting is necessary on any of the samples in the post-tested rack, and the controller is programmed to determine where to transport the post-tested rack, according to the measurement order received from the information management apparatus.

11. The sample processing apparatus according to claim 10, wherein the post-analysis rack holding section is laid between the measurement line and the skipping line.

* * * * *